(12) United States Patent
Pulitzer et al.

(10) Patent No.: US 11,437,142 B2
(45) Date of Patent: Sep. 6, 2022

(54) BIOFLUIDIC TRIGGERING SYSTEM AND METHOD

(71) Applicant: RELIANT IMMUNE DIAGNOSTICS, INC., Austin, TX (US)

(72) Inventors: Jovan Hutton Pulitzer, Frisco, TX (US); Henry Joseph Legere, III, Austin, TX (US)

(73) Assignee: RELIANT IMMUNE DIAGNOSTICS, INC., Austin, TX (US)

( * ) Notice: Subject to any disclaimer, the term of this patent is extended or adjusted under 35 U.S.C. 154(b) by 813 days.

(21) Appl. No.: 16/186,518

(22) Filed: Nov. 10, 2018

(65) Prior Publication Data

US 2019/0148014 A1 May 16, 2019

Related U.S. Application Data

(60) Provisional application No. 62/584,682, filed on Nov. 10, 2017.

(51) Int. Cl.
*G06F 3/048* (2013.01)
*G16H 50/20* (2018.01)
(Continued)

(52) U.S. Cl.
CPC ............ *G16H 50/20* (2018.01); *G16H 10/40* (2018.01); *G16H 20/10* (2018.01); *G16H 40/63* (2018.01); *G16H 40/67* (2018.01)

(58) Field of Classification Search
None
See application file for complete search history.

(56) References Cited

U.S. PATENT DOCUMENTS

| 5,587,061 A | 12/1996 | Chen |
| 5,709,788 A | 1/1998 | Chen |

(Continued)

FOREIGN PATENT DOCUMENTS

| CN | 105954512 A | 9/2016 |
| WO | 2010118124 A2 | 10/2010 |

(Continued)

OTHER PUBLICATIONS

Brown, M. C. et al. (2009). Lateral Flow Immunoassay. Tse, H. Y., Wong, R. C. (Eds.). New York, NY: Humana Press.

(Continued)

*Primary Examiner* — William C Trapanese

(57) ABSTRACT

A method of signaling a medical response action comprises receiving a biofluidic input from a client or application, by a logical testing unit, wherein the logical testing unit comprising a testing display and a persistent testing mechanism, further wherein the persistent testing mechanism comprising one or more analogical data processors, generating one or more logical results from the processing of biofluidic data from the biofluidic input, displaying, on the testing display of the logical testing unit, the one or more logical results, capturing the logical indicators on the testing display with a mobile computing unit, generating, by the mobile computing unit, a pixelated result and an action result, displaying, on the mobile display, the pixelated result and action result, responsive to a signaling input from the client or application, the mobile computing unit processes, by one or more processors, the signaling input and generating an action response packet.

12 Claims, 22 Drawing Sheets

(51) Int. Cl.
  *G16H 10/40* (2018.01)
  *G16H 40/67* (2018.01)
  *G16H 20/10* (2018.01)
  *G16H 40/63* (2018.01)

(56) References Cited

U.S. PATENT DOCUMENTS

| | | | |
|---|---|---|---|
| 5,904,826 | A | 5/1999 | Chen |
| 6,149,865 | A | 11/2000 | Hsu |
| 7,090,802 | B1 | 8/2006 | Wang |
| 7,235,098 | B2 | 6/2007 | Palmaz |
| 8,308,452 | B2 | 11/2012 | Amirouche et al. |
| 8,506,901 | B2 | 8/2013 | Chen et al. |
| 8,655,009 | B2 | 2/2014 | Chen et al. |
| 8,807,169 | B2 | 8/2014 | Amirouche et al. |
| 8,877,140 | B2 | 11/2014 | Chen et al. |
| 8,911,679 | B2 | 12/2014 | Chen et al. |
| 9,285,323 | B2 | 3/2016 | Burg et al. |
| 9,390,237 | B2 | 6/2016 | Myers et al. |
| 9,523,358 | B2 | 12/2016 | Amirouche et al. |
| 9,569,858 | B2 | 2/2017 | Babcock et al. |
| 9,607,380 | B2 | 3/2017 | Burg et al. |
| 9,726,161 | B2 | 8/2017 | Kim et al. |
| 2002/0134682 | A1 | 9/2002 | Chen |
| 2003/0207458 | A1 | 11/2003 | Sookbumroong |
| 2005/0266582 | A1 | 12/2005 | Modlin et al. |
| 2006/0014302 | A1 | 1/2006 | Martinez |
| 2006/0222567 | A1 | 10/2006 | Kloepfer et al. |
| 2006/0245933 | A1 | 11/2006 | Balch |
| 2008/0070599 | A1 | 3/2008 | Apodaca |
| 2008/0118397 | A1 | 5/2008 | Slowey |
| 2008/0235055 | A1* | 9/2008 | Mattingly ............ G16H 10/40 705/2 |
| 2009/0298191 | A1 | 12/2009 | Whitesides et al. |
| 2011/0077971 | A1 | 3/2011 | Surwit |
| 2012/0082598 | A1 | 4/2012 | Baydoun |
| 2013/0065257 | A1* | 3/2013 | Wang ................ G01N 21/31 435/7.92 |
| 2013/0161190 | A1 | 6/2013 | Ewart et al. |
| 2013/0189794 | A1 | 7/2013 | Emeric et al. |
| 2013/0273528 | A1 | 10/2013 | Ehrenkranz |
| 2014/0051173 | A1 | 2/2014 | Barstis et al. |
| 2014/0072189 | A1 | 3/2014 | Jena |
| 2014/0089006 | A1 | 3/2014 | Abreu |
| 2014/0121487 | A1 | 5/2014 | Faybishenko et al. |
| 2014/0170679 | A1 | 6/2014 | Aitchison |
| 2015/0056719 | A1 | 2/2015 | Karlovac |
| 2015/0213197 | A1* | 7/2015 | Brennan ............ C09K 11/7774 235/375 |
| 2015/0359458 | A1 | 12/2015 | Erickson et al. |
| 2016/0077091 | A1 | 3/2016 | Tyrrell et al. |
| 2016/0223536 | A1 | 8/2016 | Johnson et al. |
| 2017/0059566 | A1 | 3/2017 | Reed et al. |
| 2017/0089893 | A1 | 3/2017 | Legere, III |
| 2017/0248622 | A1* | 8/2017 | Khattak ............ H04M 1/72403 |

FOREIGN PATENT DOCUMENTS

| | | |
|---|---|---|
| WO | 2013158504 A1 | 10/2013 |
| WO | 2015143309 A1 | 9/2015 |

OTHER PUBLICATIONS

Baltekin, O., et al. (Aug. 22, 2017) Antibiotic susceptibility testing in less than 30 min using direct single-cell imaging. Proceedings of the National Academy of Sciences. 114(34).

Mudanyali, O. et al. Integrated Rapid-Diagnostic-Test Reader Platform on a Cellphone. Lab on a Chip, vol. 12, No. 15. Aug. 7, 2012; pp. 7, 12.

FisherSCI. Anti-Zika virus ELISA (IgM) test instruction. Sep. 2, 2016.

Acharya, D. et al. An ultrasensitive electrogenerated chemiluminescence-based immunoassay for specific detection of Zika virus. Scientific Reports 6, Article No. 32227. Aug. 2016.

International Search Report and Written Opinion of the International Searching Authority from PCT/US17/57037, dated Dec. 28, 2017.

International Search Report and Written Opinion of the International Searching Authority from PCT/US17/57039, dated Dec. 26, 2017.

International Search Report and Written Opinion of the International Searching Authority from PCT/US17/57041, dated Dec. 14, 2017.

International Search Report and Written Opinion of the International Searching Authority from PCT/US17/60252, dated Jan. 12, 2018.

International Search Report and Written Opinion of the International Searching Authority from PCT/US17/66528, dated Mar. 7, 2018.

Jianjun Li et al. Application of Microfluidic Devices to Proteomics Research. Journal: Molecular & Cellular Proteomics Jan. 3, 2002. 1:157-168. Canada.

Pegah N. Abadian et al. Accepted Manuscript. Book: Analytical Methods. 22pgs. Boston, MA.

Kling A. et. al. Electrochemical microfluidic platform for simultaneous multianalyte detection. Article, 2015, 916-919, Europe.

Andre Kling et al. Multianalyte Antibiotic Detection on an Electrochemical Microfluidic Platform. Article. Jul. 19, 2016, 10036-10043, Germany.

Mercier Marco. Microfluidic Continuous Flow Cell Counting and Concentration. Article. 10pgs.

Meichei Wang Kadlec et al. A Cell Phone-Based Microphotometric System for Rapid Antimicrobial Susceptibility Testing. Journal. 2014, vol. 19 (3) 258-266. Tucson, AZ.

Hongying Zhu et al. Cost-effective and compact wide-field fluorescent imaging on a cell-phone. Article. Jan. 21, 2011. 315-322, 11(2). California.

Moffitt Jeffrey R. et. al. The single-cell chemostat: an agarose-based, microfluidic device for high-throughput, single-cell studies of bacteria and bacterial communities. Article. Oct. 24, 2017. 21pgs. 12(8).

Temiz Yuksel et al. Microelectronic Engineering. Article. 2015. 156-175. Published by Elsevier B.V. Switzerland.

Vasdekis Andreas et al. Review of methods to probe single cell metabolism and bioenergetics, Journal, Jan. 20151. 115-135. Published by Elsevier.

Wang Shuqi et al. Portable microfluidic chip for detection of *Escherichia coli* produce and blood. International Journal of Nanomedicine. May 27, 2012. 2012:7 2591-2600. MA.

Hoylandm James Donaldson. Microfluidic chip and connector. Nov. 11, 2012, 16pgs. Europe.

Baltekin Ozden et al. Antibiotic susceptibility testing in less than 30 min using direct single-cell imaging. Aug. 22, 2017. 9170-9175 vol. 114-34.

Ashraf Muhammad Waseem. Micro Electromechanical Systems (MEMS) Based Microfluidic Devices for Biomedical Applications. Journal : Molecular Sciences. Jun. 7, 2011. 3648-3704.

Radenovic Aleksandra. Advanced Bioengineering Methods Laboratory Microfluidics Lab on Chip. 27pgs.

J. Hassan et al, A microfluidic biochip for complete blood cell counts at the point-of-care, Dec. 2015, 201-213, 3(4).

Kling Andre et al, Multianalyte Antibiotic Detection on an Electrochemical Microfluidic Platform, 1-3 pgs. Germany.

Au K. Anthony et al, Microvalves and Micropumps for BioMEMS, May 24, 2011, 179-220.

Sticker Drago et al, Multi-layered, membrane-integrated microfluidics based on replica molding of a thiol-ene epoxy thermoset for . . . Article, Nov. 2015, 4542-4554.

Shaegh et al, Plug-and-play microvalve and micropump for rapid integration with microfluidic chips, Article, Apr. 22, 2015, 557-564, Massachusetts, Springer Berlin Heidelberg.

Schafer Dawn et al, Microfluidic cell counter with embedded optical fibers fabricated by femtosecond laser ablation and anodic bonding, Article, Apr. 13, 2009, 17(8), 6068-6073, Colorado.

(56) References Cited

OTHER PUBLICATIONS

Hassan U. et al, A microfluidic biochip for complete blood cell counts at the point-of-care, Dec. 2015, 201-213. 3(4).

* cited by examiner

DEMOGRAPHIC I.D.

PERSONAL EMAIL

DTS (DATE/TIMESTAMP

EVRK

PRIMARY PHYSICIAN
NOTIFICATION

HEALTHCARE PROVIDER

RETAIL SUGGESTION

USER INSURANCE I.D.

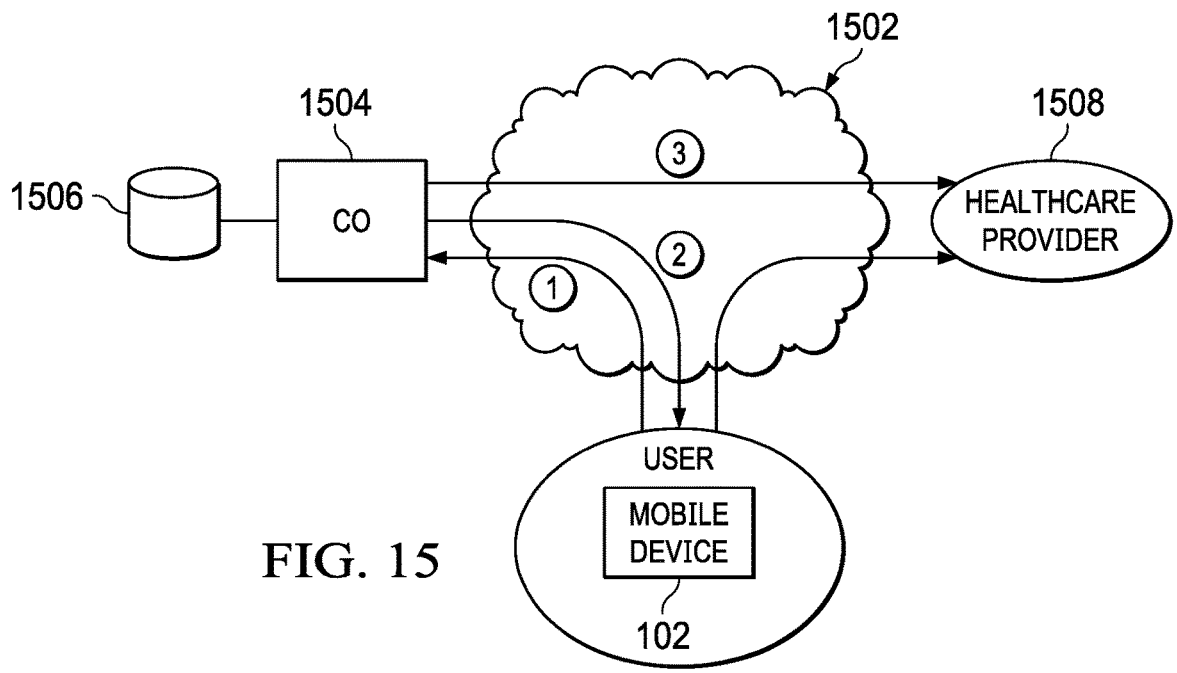
FIG. 15
| TEST RATING | HEALTH RISK | MEDICAL INTERVENTION TYPE |
|---|---|---|
| 76+ | DEADLY | EMERGENCY |
| 51-75 | DANGEROUS | URGENT |
| 26-50 | ELEVATED | NONE |
| 0-25 | NORMAL | NONE |
FIG. 16
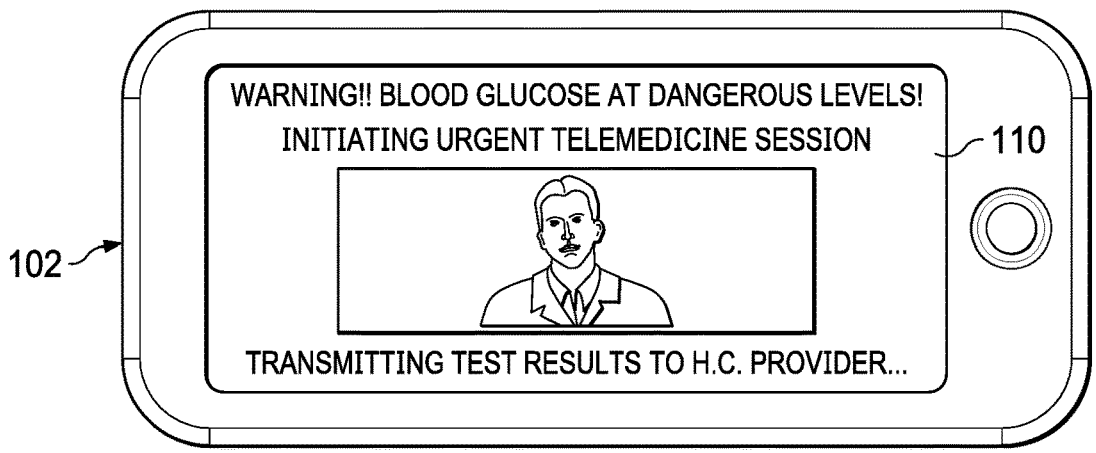
FIG. 17

| UNIQUE I.D. # XXXXX | | ← 1902 |
|---|---|---|
| NAME | JOHN DOE | ← 1904 |
| BIOLOGIC | 2402 | ← 1910 |
| BIOLOGIC | 6743 | ← 1910 |
| DOCTOR | M. FRANKLIN | ← 1906 |
| PHARMACY | MEDCO | ← 1908 |

BIOFLUIDIC TRIGGERING SYSTEM AND METHOD

CROSS-REFERENCE TO RELATED APPLICATIONS

This application claims priority to and the benefit of U.S. Provisional Application No. 62/584,682, filed Nov. 10, 2017, and entitled BIOFLUIDIC TRIGGERING SYSTEM AND METHOD, the contents of which are incorporated by reference herein in their entirety.

TECHNICAL FIELD

The following disclosure relates to a system for triggering responses to test results obtained from a biological specimen.

BACKGROUND

In today's society, people often rely on various types of tests provided within a medical professional's office to diagnosis illnesses and diseases. Currently, existing technologies for detecting illnesses and diseases often require the use of non-portable and expensive devices, as well as invasive medical tools.

SUMMARY

In one aspect thereof, a method of signaling a medical response action is provided. The method comprises receiving a biofluidic input from a client or application, by a logical testing unit, wherein the logical testing unit comprising a testing display and a persistent testing mechanism, further wherein the persistent testing mechanism comprising one or more analogical data processors and the analogical data processors comprises one or more logical keys, wherein the biofluidic input comprises biofluidic data associated with the type of input, determining whether the logical testing unit is able to process the biofluidic input by determining whether the one or more analogical data processors responds to the biofludic input, responsive to a determination that the logical testing unit is able to process the biofluidic input, processing, by the persistent testing mechanism, at least a portion of the biofluidic data of the biofluidic input, wherein the persistent testing mechanism comprises one or more persistent antibodies, generating one or more logical results from the processing of biofluidic data from the biofluidic input, displaying, on the testing display of the logical testing unit, the one or more logical results, capturing the logical indicators on the testing display with a mobile computing unit, wherein the mobile computing unit comprises a mobile display, processing, with one or more processors, the logical results on the mobile computing unit, generating, by the mobile computing unit, a pixelated result and an action result, displaying, on the mobile display, the pixelated result and action result, responsive to a signaling input from the client or application, the mobile computing unit processes, by one or more processors, the signaling input and generating an action response packet, wherein the action response packet comprises the biofluidic data, the one or more logical results, the one or more logical indictors, the pixelated result, and the action result, sending the action response packet, by one or more processors, via a network, to a central processing unit; and processing the action response packet, by one or more processors, and generating a client response action by one or more independent medical unit.

BRIEF DESCRIPTION OF THE DRAWINGS

For a more complete understanding, reference is now made to the following description taken in conjunction with the accompanying Drawings in which:

FIG. 15 illustrates an embodiment of a system which utilizes a remote diagnostic test to initiate a medical escalation and intervention;

FIG. 16 illustrates an example of a table which would be found in the database of a central office and which contains criteria for when to initiate a medical intervention based on the results of a remote diagnostic test;

FIG. 17 illustrates a mobile device from an embodiment in which a medical intervention in the form of a telemedicine session is initiated on a mobile device in response to a diagnostic test;

DETAILED DESCRIPTION

Figure 1:
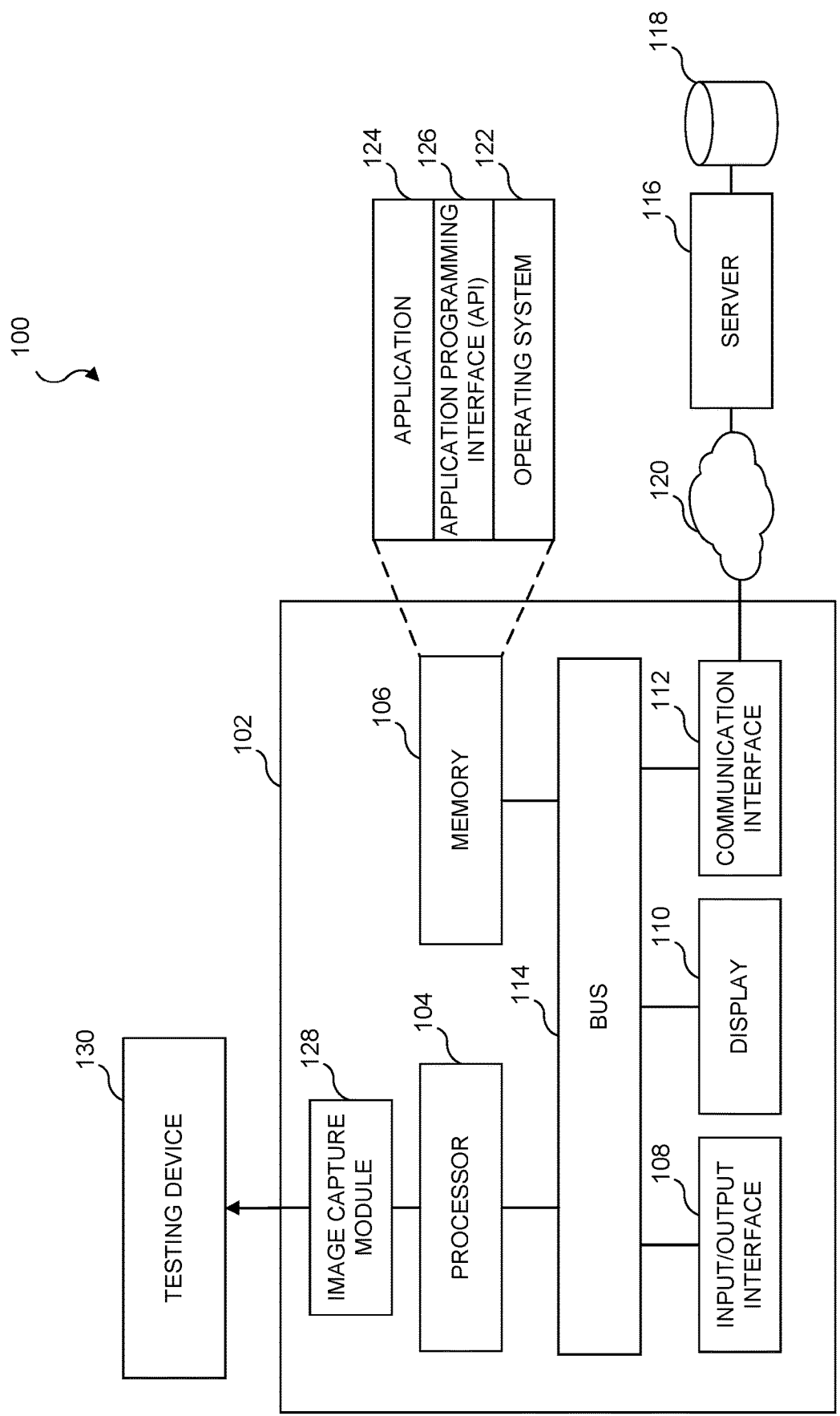
FIG. 1 illustrates a diagrammatic view of a biofluidic triggering system in accordance with various embodiments of the present disclosure.

Referring now to the drawings, wherein like reference numbers are used herein to designate like elements throughout, the various views and embodiments of a microfluidic testing system with cell capture/analysis regions for processing a parallel and serial manner is illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

In some embodiments, a biological specimen (i.e. saliva, blood, urine, semen, feces) may be provided by a user onto an analog testing device. The analog testing device may be used for testing strep (i.e. strep A, strep B, rapid strep), TP/INR, chronic conditions, MERS (Middle Eastern Respiratory Syndrome), diabetes, urinary tract infection and analysis, influenza, pregnancy, HIV, malaria, immunology, blood glucose, hemoglobin, blood electrolytes, cholesterol, fertility, troponin, cardiac markers, fecal analysis, sperm viability, food pathogens, HemoCues, CRP (put them in), dengue fever, HBA1C (put them in), Homocystein, salivary assay, drugs of abuse, drug interaction, infectious diseases, viral loads, tuberculosis, allergies (i.e. food and environment), Lyme disease, Methacillian-resistant MRSA, staphylococcus areas, sexually transmitted diseases, thyroid stimulating hormone (TSH), lipid profile, INR (put them in), TEG, magnesium, lactate, transcutaneous bilirubin, helicobacter pylori, bacteria, cell count, cancer markers, tumor markers, resistant staph aureus, antibiotic resistance, stroke markers, sepias markers, DNA markers, parathyroid, renal, or any other type of analog testing device that utilizes a biological specimen to determine a user's disease, disability, discomfort or dissatisfaction state of health. In some embodiments, the analog testing device may be compact and hand-held. In some embodiments, the analog testing device may be a standard stand-alone device.

In some embodiments, the user may take a sample of the biological specimen and transfer the biological specimen to an input of the testing device. The input of the testing device may include an input window that guides and holds the biological specimen securely within the analog testing device. In some embodiments, more than one window may be provided on the analog testing device to accommodate more than one biological specimen. For instance, the analog testing device may include two windows for a pregnancy test, in which one window may be provided to receive urine to test for the presence of HCG and a second window may be provided to receive urine to test for urinary tract infection bacteria. In some embodiments, multiple analog testing devices with one or more input windows may be used to detect the biological specimen. In some embodiments, the analog testing device may include a results display window indicating a positive or negative sign, a color spectrum, a line, a circle, a curve, a balloon, a signature marker, or variance of the like. The results may be mathematical, geometrical, color spectral, light spectrum, cell multiplication, or the like. The display window may indicate the completion of the test, an error, the test results or a combination thereof.

In some embodiments, the user may capture the results on the results display window via a mobile computing device, for instance in the form of audio, video, photo, scan, or a combination thereof. The mobile computing device may include one or more peripheral devices, for instance, an image scanner, microphone, video recorder, digital camera, speakers, and the like, to capture the results from the analog testing device and convert the results into a digital data package.

FIG. 1 illustrates a diagrammatic view of a biofluidic triggering system 100 in accordance with various embodiments of the present disclosure. The system 100 may include a mobile device 102. The mobile device 102 may be a mobile handheld user device, such as a smart phone, tablet, or the like. The mobile device 102 may include a processor 104, a memory 106, an input/output (I/O) interface 108, a display 110, and a communication interface 112 all connected via a bus 114. The communication interface may connect the mobile device 102 to outside sources, such as a server 116 having a database 118 associated therewith, over a network 120, i.e. a cellular network or Internet network. The memory 106 may store an operating system 122 and various special-purpose applications, such as a browser by which webpages and advertisements are presented, or special-purpose native applications, such as weather applications, games, social-networking applications, shopping applications, and the like. The digital data package may provide data to a special purpose native application 124 stored in the memory 106, the application 124 having associated therewith an application programming interface (API) 126. The digital data package may be obtained by the mobile device 102 by an image capture module 128 connected to the processor 104. The image capture module 128 may capture an image, scan, video, or other digital media of a testing device 130, converting the analog biologic sample testing device and the results presented on the device to a digital format and to create a unique identifier that can be used to trigger a plurality of events.

The unique identifier comprising the digital data package may be analyzed by the application 124 to determine the results from the analog testing device. In some embodiments, the determination of the test results, due to the type of analog testing device, is not determined locally by the application 124. In some embodiments, the unique identifier may be transmitted to the server 116, via the network 120, for remote analysis of the data contained in the unique identifier. In some cases, results from the analog testing device may be determined locally and remotely. In some instances, the user of the mobile device 102 may not have cellular network or Internet connection, for instance, the settings for connectivity on the mobile device 102 is disabled, turned off or a combination thereof. In this case, the transmission of the unique identifier to the server 116 may be postponed until a connection is available.

In some embodiments, the mobile device 102 may include a location sensor, such as a global positioning system (GPS) sensor or other components by which geographic location is obtained, for instance, based on the current wireless environment of the mobile device 102, like SSIDs of nearby wireless base stations, or identifiers of cellular towers in range. In some cases, geographic locations are inferred by, for instance, an IP address through which a given mobile device 102 communicates via the Internet, which may be a less accurate measure than GPS-determined locations. In other cases, geographic location is determined based on a cell tower to which a mobile device 102 is wirelessly connected. Depending on how the geographic data is acquired and subsequently processed, that data may have better or less reliable quality and accuracy.

Figure 2:
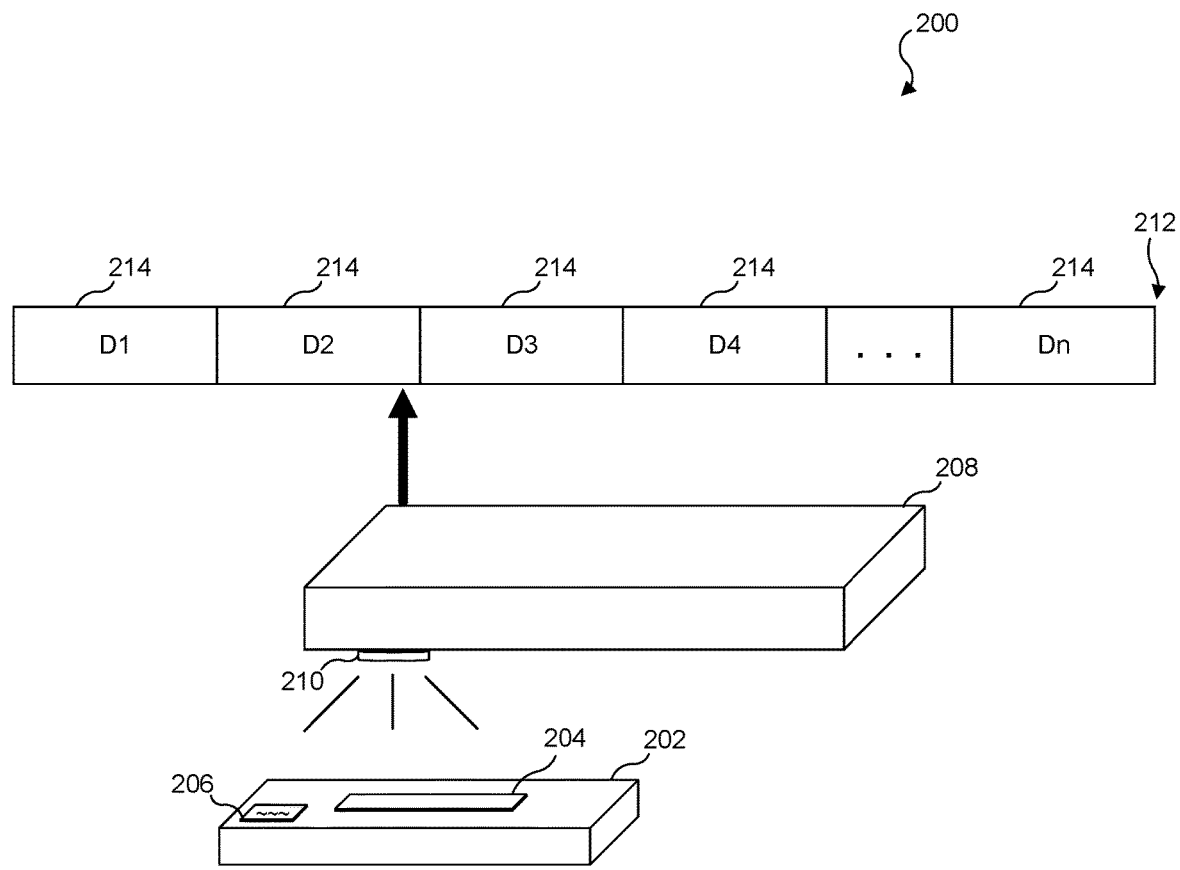
FIG. 2 illustrates a diagrammatic view of an analog testing device to a digital format and unique identifier conversion process.

FIG. 2 illustrates a diagrammatic view of an analog testing device to a digital format and unique identifier conversion process 200 in accordance with various embodiments of the present disclosure. A testing device 202 may provide medical test results in an analog format, such as in a results display window 204 indicating a positive or negative sign, a color spectrum, a line, a circle, a curve, a balloon, a signature marker, or variance of the like. A biologic specimen may be deposited into the testing device 202 where the biologic may bind or react with particular reagents specific to the type of test to which the testing device 202 pertains. The testing device 202 may also include a test type identifier 206, such as a code, graphic, symbol, or other indicator on a surface of the testing device 202.

A mobile device 208, which may be the mobile device 102 described herein, may include a capture device 210. The mobile device 208 may convert use the capture device 210, in addition to other data known or otherwise obtained by the mobile device 208, to convert the analog data and biologic presented by the testing device 202 to a digital unique identifier 212. When digital media such as an image, video, or other digital format of the testing device 202 is captured by the capture device 210, certain properties may be analyzed, processed, and stored into as a digital data package. For instance, the test type associated with the testing device 202 may be determined by the mobile device 208 by identifying the particular test associated with the test type identifier 206 captured within the digital media.

Test results provided in the results display window 204 or elsewhere on the testing device 202 may also be captured within the digital media and analyzed. For example, in the case of a color indicator as the result of the test, the RGB values of the pixels contained in the digital media of the test results may be determined in order to provide a digital value for the test results. The test result may be stored in the digital data package in a particular digital format, for instance, a positive or negative test result value. The value may be a binary value, a rating, a probability, or other type of result indicator. The biologic specimen used to conduct the test may also be included in the digital data package. The biologic specimen provided into the testing device 202 may be determined from the test type identifier 206, since in many cases the specific test will dictate the biologic to be used.

The data provided by the digital data package may also include the type, manufacture and serial number of the testing device 202, and a timestamp for when the capture device 210 captured the digital media. The manufacture, serial number and cellular provider of the mobile device 208 may also be included in the digital data package. The application 124 may then generate the unique identifier 212 from the data of the testing device 202 and mobile device 208, in combination with data of the user of the mobile device 208. Data of the user may be the user's name, birthday, age, gender, social security number, height, weight, race, diagnosis status, insurance information, medical codes, drug codes, and the like, and a combination thereof.

In some embodiments, the unique identifier may be verified by a verification server, such as the server 116, to determine the authentication of the biological specimen. In some cases, the user may provide the analog testing device 202 with a substance not classified as a biological specimen. In this instance, an application on the server 116 will provide the application program interface 110 with a message indicating an error, in which the user may be required to provide a biological specimen to a different analog testing device. In some embodiments, after verification of a biological specimen, the local application program 124 or the server 116 via the user's application program 124 will provide the user with a positive or negative outcome of the analog testing device 202. In some cases, the user is displayed a negative test result and the application program 124 of the mobile device 208 indicates that testing is completed. In other cases, the user is displayed a positive test result by the application program 124 on the display 110 of the mobile device 208.

The unique identifier 212 may include of a plurality of digital data streams 214 used during creation of the unique identifier 212, such as information included within the digital data package, or otherwise known or obtained by the mobile device 208 or the server 116. The plurality of digital data streams 214 (D1, D2, D3, D4 . . . Dn) may be assembled together to create the unique identifier 212, and the mobile device 208, the server 116, or the authorized system components may parse or deconstruct the unique identifier 212 to analyze specific user properties or test properties, and to trigger events based on the properties.

Creating a single unique identifier 212 which contains many different items of information is an efficient way of associating many different types of information with a single biologic, user, test, etc. Every time a test is conducted, a new unique identifier 212 may be created. Each unique identifier created may include the plurality of data streams 214. Each one of the plurality of data streams 214 in the unique identifier 212 stores a different type of information. In some embodiments, the information stored in data streams 214 includes the test type, the test results, demographics of the user, or an identification number, such as an IMSI number, for the mobile device 208. Different embodiments may include different data streams 214, as is described hereinbelow with respect to FIGS. 4A-4K. In some embodiments, the unique identifier 212 is set up in a structural format, such that each data stream 214 is a subcomponent of the unique identifier 212. In some embodiments, unique identifier 212 is a string of alphanumeric characters, and the data streams 214 which make up the unique identifier 212 are simply different portions of the character string. In these embodiments, the format of the unique identifier 212 is known to a database or server which can correctly parse the unique identifier 212 into the separate data streams 214 for analysis.

Figure 3:
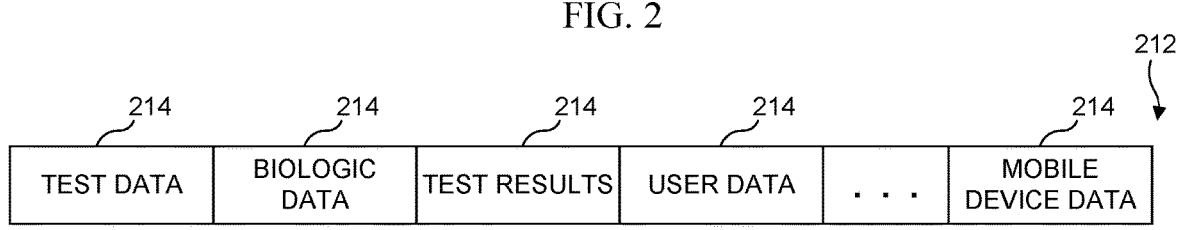
FIG. 3 illustrates one example of a unique identifier 302 in accordance with various embodiments of the present disclosure.

FIG. 3 illustrates one example of a unique identifier 302 in accordance with various embodiments of the present disclosure. In this example, the plurality of data streams 212 includes, but is not limited to, test data, such as test type, biologic data, such as biologic type or types used by the test, test results obtained upon completion of the test, user data such as demographics, and mobile device data, such as an IMSI number.

Figure 4A:
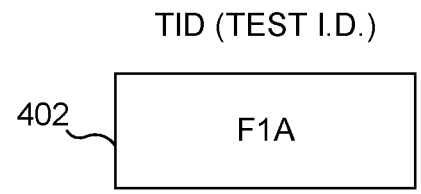
FIG. 4A illustrates an embodiment in which one of the data streams of the unique identifier is a test identification, TID field.

Referring now to FIG. 4A, there is illustrated an embodiment in which one of the data streams 214 of the unique identifier 212 is a test identification, TID data stream 402. The TID data stream 402 identifies the type of test which the user is conducting (pregnancy, HIV, peanut allergy, etc.). In the example depicted in FIG. 4A, the TID data stream 402 is a character string of "F1A," which indicates that the test is for the flu, is test version "1," and is a test of an example "A" type of flu substrain. Different embodiments of TID data stream 402 will have different sizes of character strings, or will not be character strings at all. In some embodiments, this information is obtained when a user uses the mobile application to scans a barcode or image from the test product, or when the user inputs an identification code into the mobile application. In some embodiments, the data in the TID data stream 402 is used by the mobile application to determine which database to access when processing the results of the medical test.

Figure 4B:
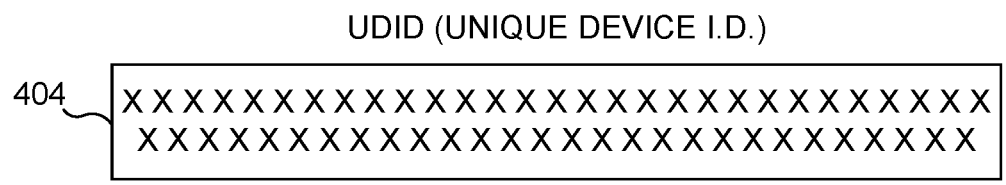
FIG. 4B illustrates an embodiment in which one of the data streams of the unique identifier is a unique device identification, or UDID field.

Referring now to FIG. 4B, there is illustrated an embodiment in which one of the data streams 214 of the unique identifier 212 is a unique device identification, or UDID data stream 404. The UDID data stream 404 contains information which uniquely identifies the mobile device on which the application is running. Many devices, such as mobile phones, have unique identifiers built-in by the manufacturer, often in the form of long character strings, such as an IMSI number. In some embodiments, the UDID data stream 404 is a character string which includes such an identifier. In other embodiments, the UDID 404 is generated by the mobile application or the mobile application user.

Figure 4C:
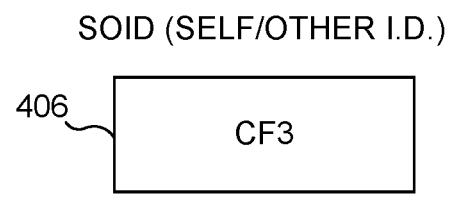
FIG. 4C illustrates an embodiment which includes a SOID (self/other identification) field.

Referring now to FIG. 4C, there is illustrated an embodiment which includes a SOID (self/other identification) data stream 406. The SOID data stream 406 is a data stream 214 which designates whether the medical test is being performed on the mobile application user, or whether the test is being performed on an individual other than the user. The SOID data stream 406 also identifies the relationship between the person being tested and the mobile application user. Some embodiments also include basic demographic data, such as gender or age range, in the SOID data stream 406. For example, if the person being tested is a small child, then the actual user of the mobile application may be the child's mother or father. In the example depicted in FIG. 4C, the SIOD data stream 406 is a character string which reads "CF3," which indicates that the person being tested is a child of the mobile application user, is female, and is three-years-old. Naturally, other embodiments will have different formats for the SOID data stream 406, and may not be character strings.

Figure 4D:
FIG. 4D illustrates an embodiment which includes a data stream which contains demographic information.

Referring now to FIG. 4D, there is illustrated an embodiment which includes a data stream 2302 which contains demographic information. A DEMZIP data stream 408 (demographic/ZIP code) contains information about the person being tested with the medical test. In the example illustrated in FIG. 4D, the DEMZIP data stream 408 includes a character string which represents the gender, age range, and geographic location (in the form of a ZIP code) of the person being tested. For example, in FIG. 4D, the DEMZIP data stream 408 indicates that the test subject is a male, in age range 4, who is located in the ZIP code 78237. In other embodiments, the DEMZIP data stream 408 will have additional demographic traits included, such as height or weight. Some embodiments will contain geographic location information in a format other than ZIP code, such as city, state, or country names. In some embodiments, such as is illustrated in FIG. 4D, the DEMZIP data stream 408 will be a character string, while in other embodiments, it will take other forms.

Figure 4E:
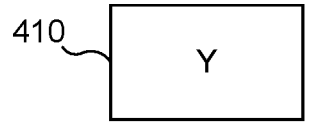
FIG. 4E illustrates an embodiment in which the unique identifier contains a data stream which indicates whether or not the user has supplied their personal email address.

Referring now to FIG. 4E, there is illustrated an embodiment in which the unique identifier 212 contains a data stream 214 which indicates whether or not the user has supplied their personal email address. A personal email data stream 410 does not actually contain the email address of the user, but it does indicate whether or not the user has supplied an email address to the mobile application. In some embodiments, if personal email data stream 410 indicates that the user has supplied an email address, then when the unique identifier 212 is passed to a remote server, the remote server will link the unique identifier 212 with the email address of the user which has been stored in a separate database. In some embodiments, such as illustrated in FIG. 4E, the personal email data stream 410 is a simple character string of "Y" or "N" to indicate "yes" or "no" with regard to whether an email has been supplied. Other embodiments will have a "1" or a "0" for "yes" or "no" or may have other character strings or data formats.

Figure 4F:
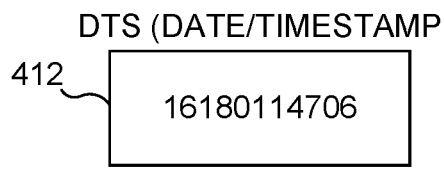
FIG. 4F illustrates an embodiment of a data stream for a unique identifier which contains a timestamp of when a completed medical test is scanned or photographed by the mobile application.

Referring now to FIG. 4F, there is illustrated an embodiment of a data stream 214 for a unique identifier 212 which contains a timestamp of when a completed medical test is scanned or photographed by the mobile application. Knowing exactly when a medical test was scanned by a mobile application can be very important in different types of analysis. In this embodiment, the DTS data stream (date/time stamp) 412 indicates the time in a YYMMDDHHMMSS format, that is, the first two characters indicate the year, the next two indicate the month, the next two indicate the day, the next two indicate the hour (in a 24-hour day format), the next two indicate the minute, and the last two indicate the second. Naturally, some embodiments will have other formats for the DTS data stream other than a 12-character string, and will have different levels of specificity with regard to the time.

Figure 4G:
FIG. 4G illustrates a data stream for an embodiment in which a unique identifier contains information related to the results of a medical test.

Referring now to FIG. 4G, there is illustrated a data stream 214 for an embodiment in which a unique identifier 212 contains information related to the results of a medical test. These embodiments will have test results, or information related to test results as part of the overall unique identifier 212 as an EVRK (Evaluation of Results and Ranking of the Diagnosis) data stream 414, as opposed to, or in addition to, the results being in a totally separate file. In embodiments of the system which use numerical values for test results, these values will be incorporated into the EVRK data stream 414. Some embodiments will also include an escalation scale, which is a numerical indication, as a number on a predetermined scale, of how urgent or serious a potential medical problem might be. In the example illustrated in FIG. 4G, the EVRK data stream 414 is a character string and has a value of "0982," with the first three digits representing the results of the test and the last digit representing the escalation scale value. Other embodiments will have other formats for the EVRK data stream 414 and will have the results indicated in other ways, such as alphanumerically, rather than just numerically.

Figure 4H:
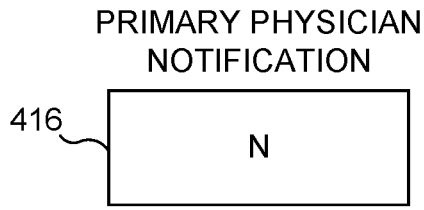
FIG. 4H illustrates a data stream for an embodiment in which a unique identifier includes an indication of whether or not the user wishes to have the test results sent to a healthcare provider.

Referring now to FIG. 4H, there is illustrated a data stream 214 for an embodiment in which a unique identifier 212 includes an indication of whether or not the user wishes to have the test results sent to a healthcare provider. In these embodiments, the unique identifier 212 includes a PDr (personal doctor) data stream 416. The PDr data stream 416 is simply an indication of whether or not the user wishes to have the test results transmitted to the user's healthcare provider. In some embodiments, a user inputs this preference into the mobile application after completing the medical test, while in other embodiments, this preference is input into the mobile application separately from any particular test. In some embodiments, an indication of wanting the results sent to the healthcare provider will initiate a telemedicine session with the healthcare provider. In some embodiments, such as that which is illustrated in FIG. 4H, the PDr data stream 416 is a short, simple character string, such as "Y," "N," "1," or "0." Other embodiments will have different formats.

Figure 4I:
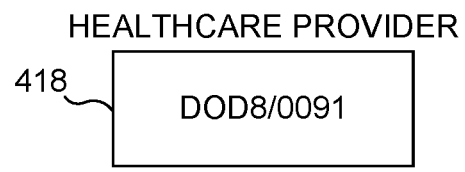
FIG. 4I illustrates a data stream for an embodiment in which a unique identifier includes information identifying the user's healthcare provider.

Referring now to FIG. 4I, there is illustrated a data stream 214 for an embodiment in which a unique identifier 212 includes information identifying the user's healthcare provider. In these embodiments, the unique identifier 212 includes a Healthcare Provider data stream 418. The Healthcare Provider data stream 418 includes information which can be used in a storage database to look up the healthcare providers identification and contact information. This information would be used in situations where the mobile application user indicates that they wish to have the medical test results sent to the healthcare provider. In some embodiments, the Healthcare Provider data stream 418 contains a code which is used to look up more detailed information from another storage database, while in other embodiments, the identification information and the contact email address or phone number is stored in the data stream itself.

Figure 4J:
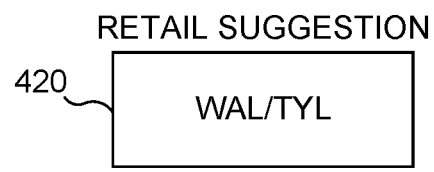
FIG. 4J illustrates a data stream for an embodiment in which a unique identifier includes information relating to a retail suggestion.

Referring now to FIG. 4J, there is illustrated a data stream 214 for an embodiment in which a unique identifier 212 includes information relating to a retail suggestion. For these embodiments, a Retail Suggestion data stream 420 is included in the unique identifier 212. The Retail Suggestion data stream 420 includes data which identifies a retailer or a product or service which can be suggested (for example, through the mobile application) to a user. In some embodiments, these suggestions are based on the type of medical test performed. In other embodiments, the suggestions are based on the results of the medical test. For example, if the medical test is a pregnancy test which returns a positive result, then the suggestion might be for a brand of baby diapers. In the example illustrated in FIG. 4J, the Retail Suggestion data stream 420 provides a suggestion of Tylenol ("TYL") which can be purchased at Walgreens ("WAL"). In the example illustrated in FIG. 4J, the Retail Suggestion data stream 420 is a character string. In other embodiments, the format of the Retail Suggestion data stream 420 will be different. In some embodiments, the Retail Suggestion data stream is utilized in situations where the PDr data stream 416 indicates that the user does not wish to have the test results communicated to a healthcare provider.

Figure 4K:
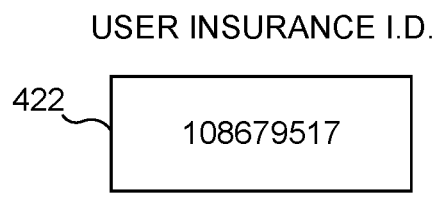
FIG. 4K illustrates a data stream for an embodiment in which a unique identifier includes information identifying the user's insurance I.D.
Figure 5A:
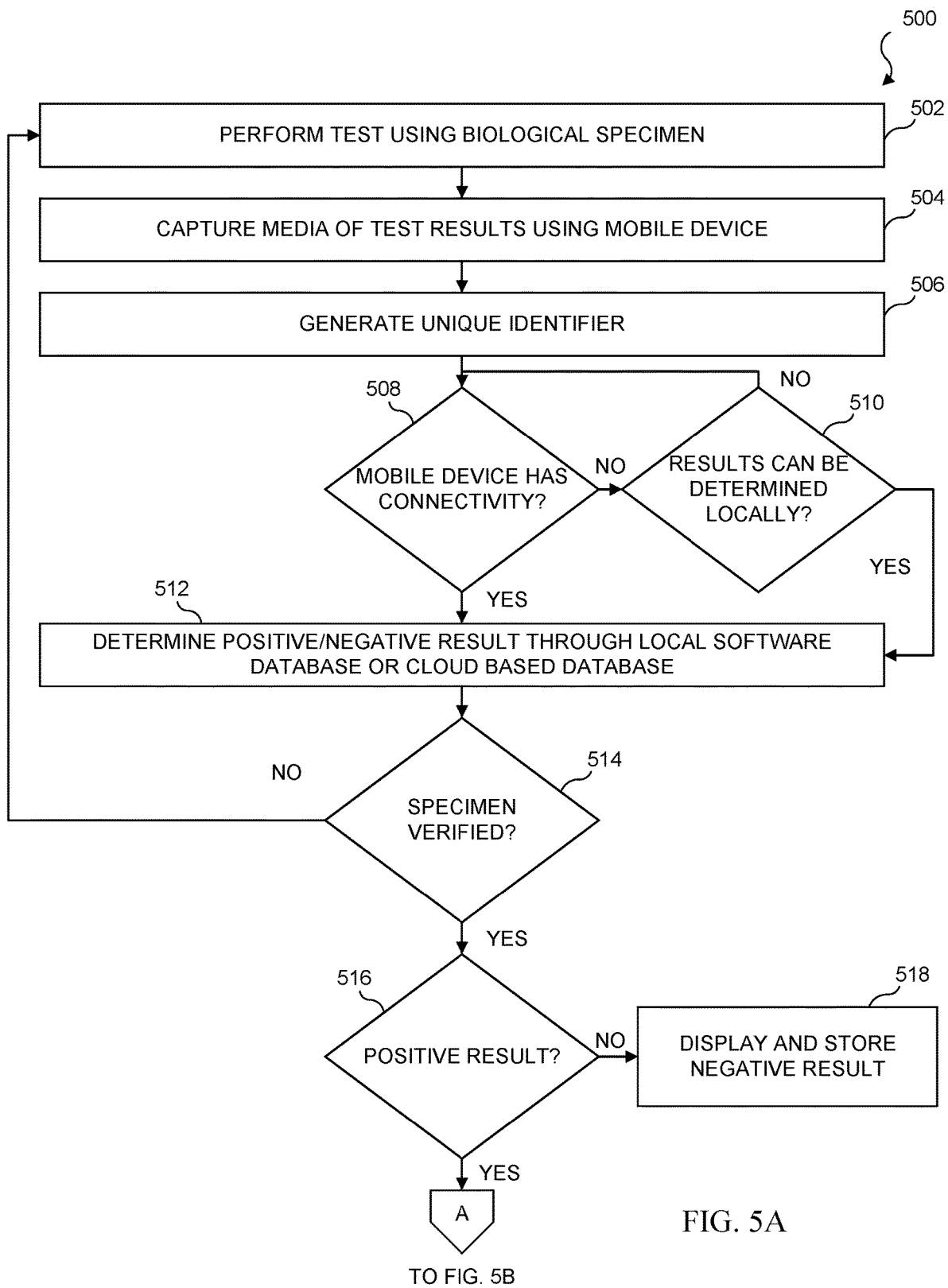
FIGS. 5A-5D illustrate a biofluidic triggers process.
Figure 5B:
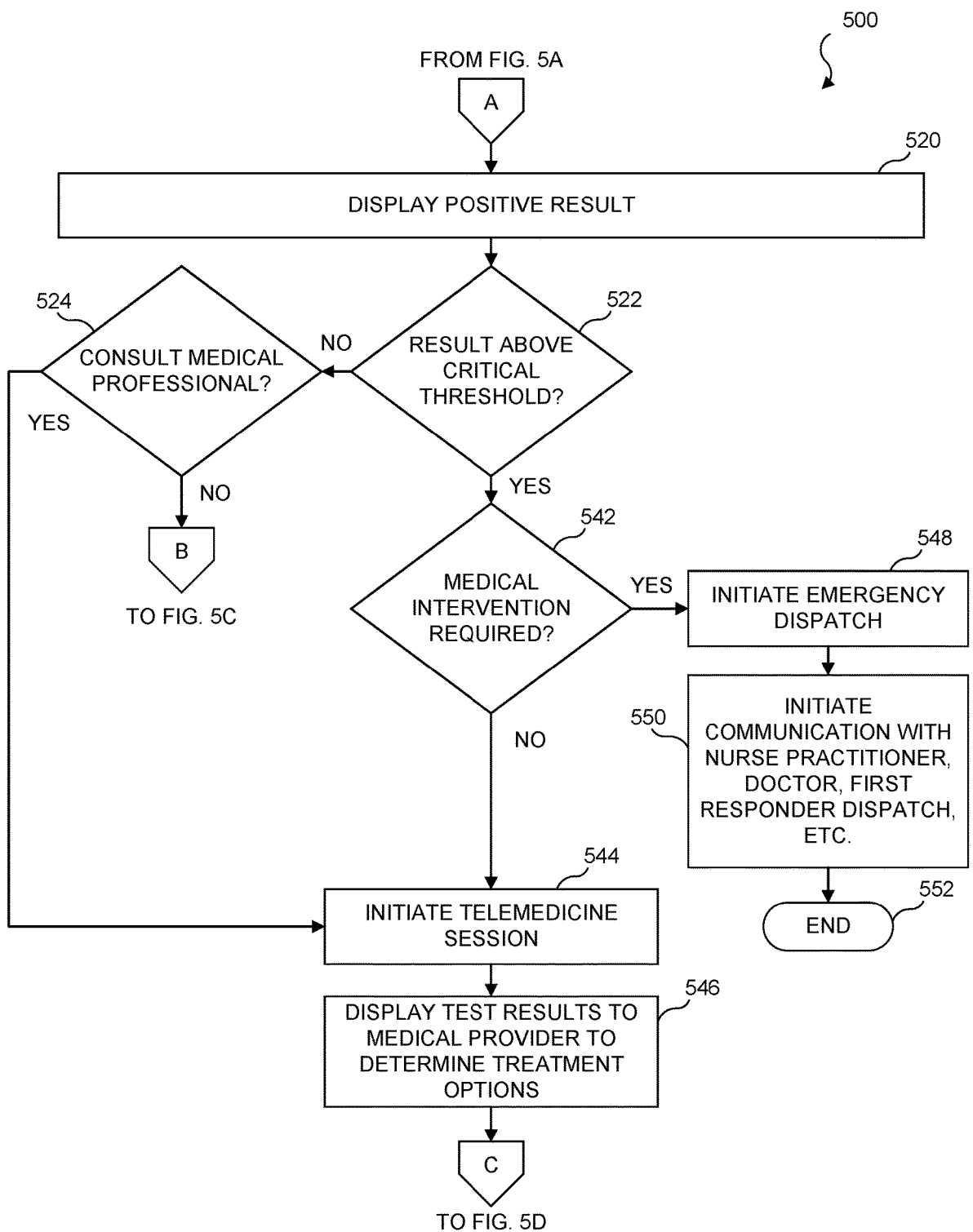
Figure 5C:
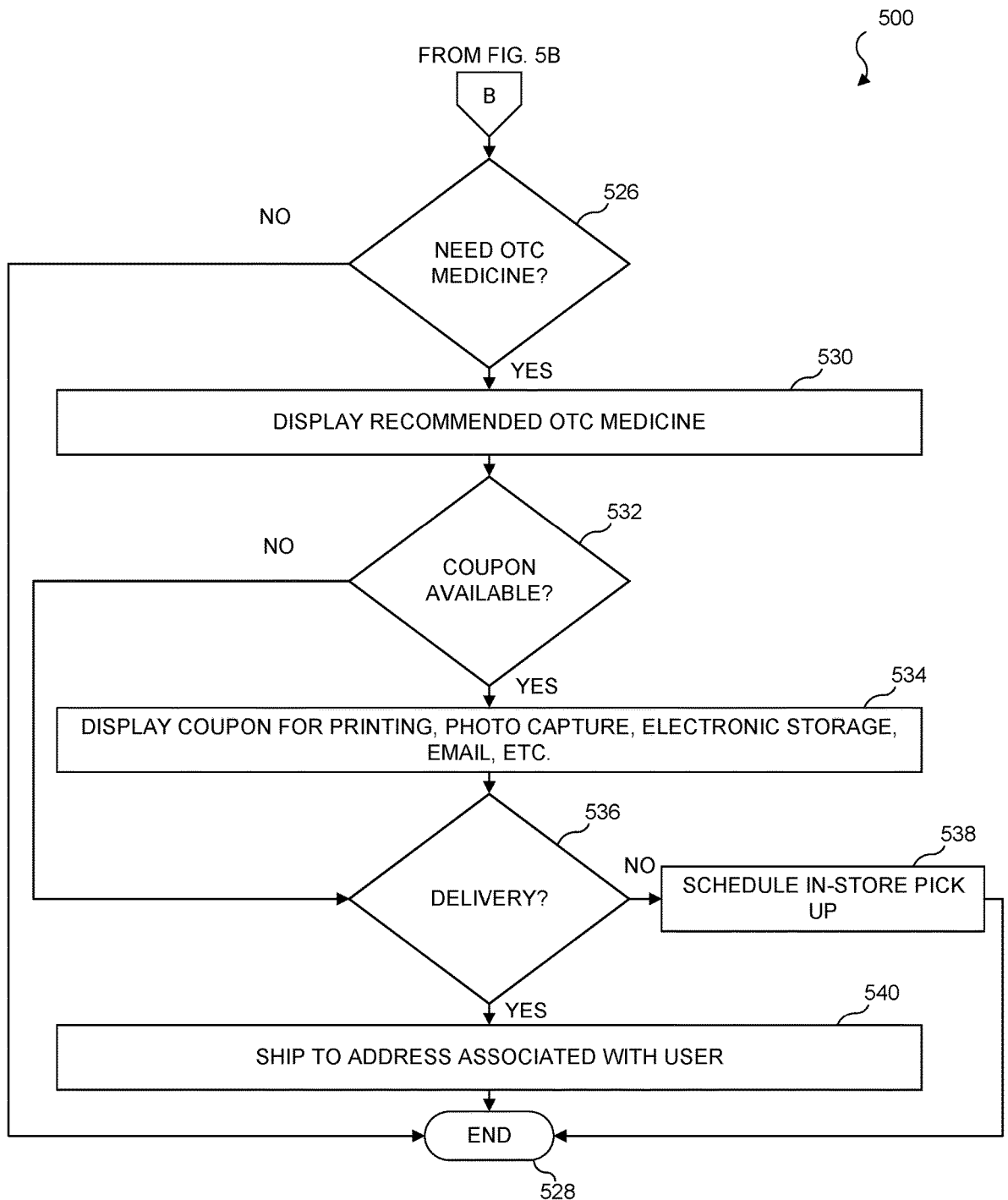
Figure 5D:
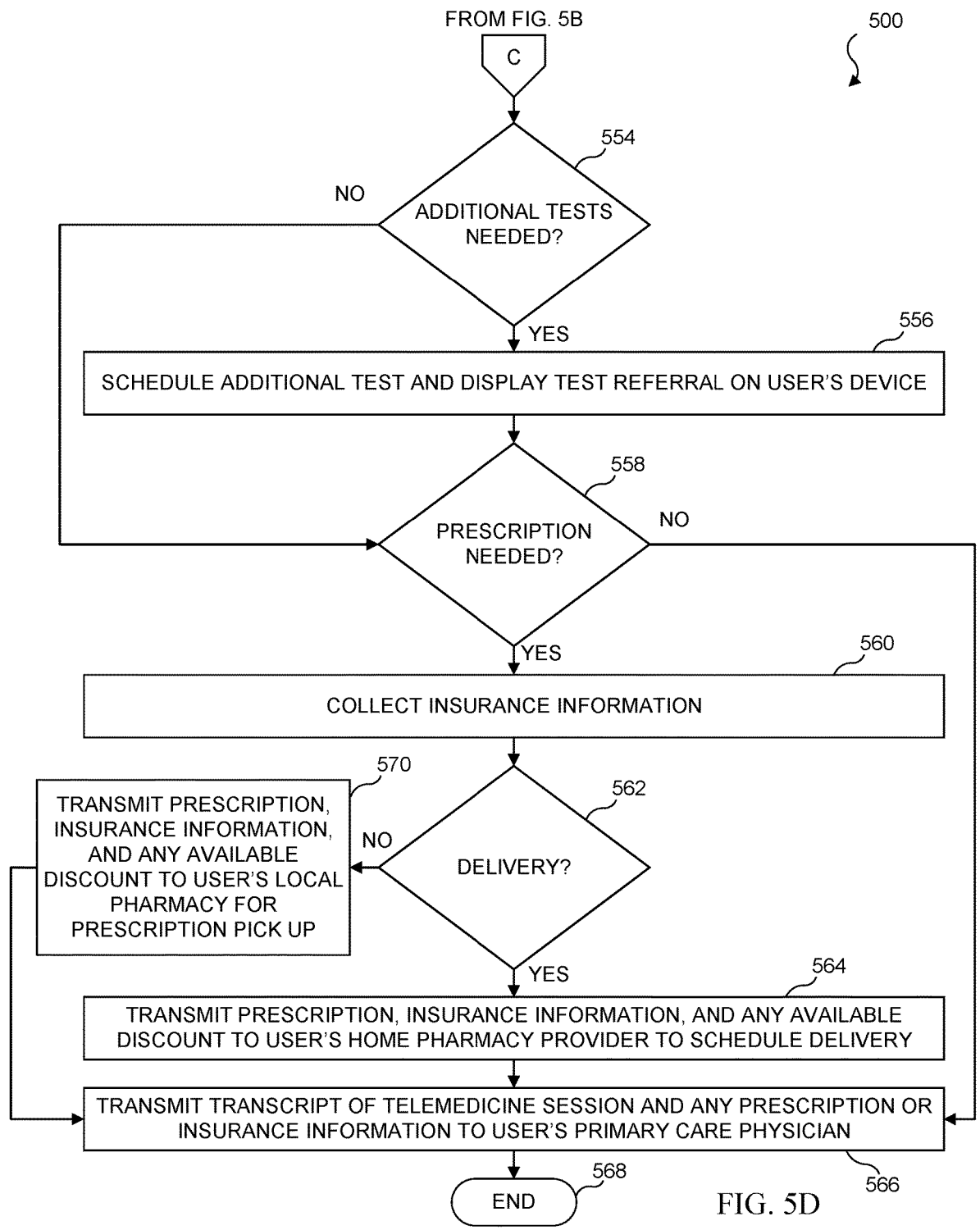

Referring now to FIG. 4K, there is illustrated a data stream 214 for an embodiment in which a unique identifier 212 includes information identifying the user's insurance I.D. In these embodiments, the unique identifier 212 includes an insurance I.D. data stream 422. The insurance I.D. data stream 422 includes information which can be used in a storage database to look up a user's insurance information. This information would be used in situations where the mobile application user indicates that they wish to have the medical test results sent to the healthcare provider, pharmacy, or other entity to allow the user's insurance to be used for a transaction, such as filling a prescription.

Referring now to FIGS. 5A-5D, there is illustrated a biofluidic triggers process 500. The process 500 begins at step 502 where a test using a logical testing unit is performed with a biofluidic input received from a user, client, or application. The logical testing unit may include a testing display and a persistent testing mechanism, and the persistent testing mechanism may include one or more analogical data processors, and one or more persistent antibodies. The analogical data processors may include one or more logical keys. At step 504, media of test results produced by the testing unit may be captured, such as by a mobile device such as the mobile device 102. The biofluidic input may include or be converted digitally to include biofluidic data associated with the type of biofluidic input. The analogical results provided by the testing device or logical testing unit may be first displayed on the display 110 of the mobile device 102 before digital conversion is performed.

At step 506, a unique identifier is generated in accordance with that described herein. At decision block 508, it is determined whether the mobile device has connectivity, such as WiFi or cellular data connectivity to the network 120. If not, the process flows to decision block 510 where it is determined whether the results can be determined locally by the mobile device. In some embodiments, the results of certain biological specimen tests may be able to be determined by the mobile device alone, such as a urinary tract infection (UTI) test. If the test cannot be performed locally by the mobile device, the process loops back to decision block 508 to again check for connectivity. If at step 508 it is determined that the device has connectivity, or if at step 510 it is determined that the test results can be determined locally, the process flows to step 512.

At step 512, the results of the test are determined, either locally be the mobile device or by a remote source such as the server 116 or the database 118. At decision block 514, as described herein, the biofluidic input may be verified by a verification server, such as the server 116, to determine the whether the one or more analogical data processors should respond to the biofluidic input. This verification may be used to determine if any specimen was applied at all, if only water was applied, etc. If verification cannot be made, the process 500 loops back to step 502 to have the test performed again. If the specimen is verified, the process moves to decision block 516. At decision block 516, it is determined whether the results of the test are positive. If not, the process flows to step 518 where a negative result is displayed to the user and stored on the server 116 and/or database 118. If at decision block 516 the results are positive, the process flows to step 520 to display the positive result on the mobile device.

At decision block 522, it is determined whether the positive result is above a critical threshold. If not, the process 500 flows to decision block 524, where it is determined whether the user wants to consult a medical professional. If not, the process flows to decision block 526, where it is determined whether the user needs or wants over-the-counter (OTC) medicine. If not, the process ends at end block 528. If so, the process flows to step 530, where one or more recommended OTC medications may be displayed to the user. In some embodiments, a prescription may not be required and an over-the counter (OTC) remedy or medicine is displayed on the client's application program interface. In some embodiments, the application program interface may display to the user an advertisement, discount or coupon to the user for the OTC remedy or medicine during the telemedicine session. In this instance, the medical professional may input a client data package into the application program interface of the professional's mobile device 102. The client data package may include the OTC information, summary of health report, address of the client, phone number of the client, recommendation of follow up with primary care physician, and diagnosis. In some embodiments the client data package is transmitted to the content server, via the network, and saved to the database corresponding to the unique identifier of the user. In some embodiments, the content server may then transmit the client data package to the user's application program interface to display to the user.

At decision block 532 it is determined whether a coupon is available for the one or more recommended OTC medications. In some embodiments, the application program interface may display to the user an advertisement, discount or coupon to the user for the OTC referred during the telemedicine session. In some instances, the client's application program interface may display information to gather flexible spending account information of the client. If so, the process flows to step 534 to display the coupon on the mobile device to allow the coupon to be printed, photo captured such as by taking a screenshot, saved electrically, emailed, etc. The process then flows to decision block 536. If at decision block 532 it is determined that a coupon is not available, the process also then flows to decision block 536. At decision block 536, it is determined whether delivery of the OTC medication is to be made to the user. If not, the process flows to step 538 where in-store pick up is scheduled, the process then flowing to end block 528. If at decision block 536 it is determined that the OTC medication is to be delivered to the user, the process flows to step 540 where the OTC medication is shipped to an address associated with the user, the process then flowing to end block 528. In some embodiments, the client data package, discount or coupon for the prescription, the medical insurance information, or a combination thereof, may be transmitted to a retail store server. The retail pharmacy server may be one of CVS, Walgreens, Target, Walmart, grocery store, Amazon, Amazon Prime Now, and the like. In some embodiments, the prescription may be delivered to the client via delivery services, for instance, Uber, Lyft, and the like. In some embodiments, the prescription may be delivered to the client via delivery services, for instance, Uber, Lyft, and the like.

If at decision block 522 it is determined that the positive result is above a critical threshold, the process flows to decision block 542. At decision block 542, it is determined whether medical intervention is required due to the result being above the critical threshold. If not, the process flows to step 544. If back at decision block 524, it is determined that the user, after it is determined that the result is not above a critical threshold, does not want to consult with a medical professional, the process also then flows to step 544. At step 544, a telemedicine session is initiated. The process then flows to step 546, where the positive test results are displayed to a medical provider so that the medical provider may determine treatment options. In some embodiments, the result from the analog testing device is below a test threshold. In this instance, the user may initiate a telemedicine session with a medical professional via a mobile device 102 with an application program interface. In some embodiments, the user is displayed on the application program interface a medical professional to conference with via the mobile device's audio and video device, i.e. the camera, microphone, speaker, LCD display screen or the like. In some embodiments, the medical professional may authenticate the user and the test results from the analog testing device, gather medical history information from the user, discuss the results of the test with the user, provide medical suggestions based on the results from the testing device and the user's medical history, suggest prescriptions options as a result of the information gather, and the like.

If at decision block 542 it is determined that medical intervention is required, the process flows to step 548 to initiate an emergency dispatch. In some embodiments, the results from the analog testing device may indicate a medical emergency and medical intervention of the medical emergency may occur. In this instance the result from the analog testing device was above a test threshold, which indicates a medical risk. In some cases, medical intervention may be contacting 911, contacting emergency contact, contacting an ambulance service, i.e. private and public services, and the like, via the application program interface. In some instances, the user may be displayed a result on the mobile device 102 that medical intervention has occurred and may be placed in direct contact with 911 dispatch, the emergency contact or the private or public ambulance service. In some embodiments, once medical intervention is indicated, the user may be prevented from ending the testing session. In other instances, the user may be required to provide consent to end the session. Consent may include signing a waiver, creating a digital pin for authentication to electronical sign a waiver or recording a voice message, all indicating consent to end the session without medical intervention. At step 550, while emergency dispatch is en route or even after emergency dispatch arrives, a communication may be initiated between the user and a nurse practitioner, doctor, first responder dispatch, etc., in order to assure the user or walk the user through steps the user may need to perform. The process then ends at step 552. Steps 548 and 550 may in some embodiments be initiated automatically, while not allowing the user to bypass the option, due to the detected critical nature of the user's health.

After step 546, the process flows to decision block 554. At decision block 554, it is determined by the medical provider conducting the telemedicine communication with the user whether one or more additional tests are needed. If so, the medical provider schedules the one or more additional tests, and one or more referrals regarding the additional tests are displayed on the user's device. The process then flows to decision block 558. If at decision block 554 it is determined that additional tests are not needed, the process also then flows to decision block 558.

At decision block 558, it is determined whether a prescription is needed. In some cases, the medical professional may prescribe a medicine in response to the user's telemedicine session. In this instance, the medical professional may input a client data package into the application program interface of the professional's mobile device 102. The client data package may include the prescription information, summary of health report, address of the client, phone number of the client, recommendation of follow up with primary care physician, and diagnosis. In some embodiments the client data package is transmitted to the server 112, via the network 116, and saved to the database corresponding to the unique identifier of the user. In some embodiments, the content server may then transmit the client data package to the user's application program interface for display to the user. If it is determined at decision block 558 that a prescription is needed, at step 560, insurance information pertaining to the user may be collected.

In some embodiments, the application program interface may display to the user an advertisement, discount or coupon to the user for the prescription prescribed during the telemedicine session. In some instances, the client's application program interface may display information to gather medical insurance information of the client. In some instances, the client's application program interface may display information to gather flexible spending account information.

At decision block 562, it is determined whether delivery of the prescription is to be made. If delivery is to be made, the process flows to step 564. At step 564, in some embodiments, the client data package, discount or coupon for the prescription, the medical insurance information, or a combination thereof, may be transmitted to a prescription home delivery server. In this instance, the prescription home delivery server may initiate a home delivery provider to initiate a delivery of the prescription to the client. In some embodiments, the prescription may be delivered to the client via delivery services, for instance, Uber, Lyft, and the like. The process then flows to step 566 to transmit a transcript of the telemedicine session and any prescription or insurance information to the user's primary care physician. The process then ends at end block 568.

If at decision block 558 it is determined that a prescription is not needed, the process flows to step 566 and to end block 568. If at decision block 562 it is determined that delivery of the prescription is not to be made, the process flows to step 570. At step 570, prescription and insurance information, and any available discount, are transmitted to the user's local pharmacy for prescription pick up. In some embodiments, the client data package, discount or coupon for the prescription, the medical insurance information, or a combination thereof, may be transmitted to a retail pharmacy server. The retail pharmacy server may be one of CVS, Walgreens, Target Pharmacy, Walmart Pharmacy, hospital pharmacies, grocery store pharmacies, and the like. The process then flows to step 566 and end block 568.

Figure 6:
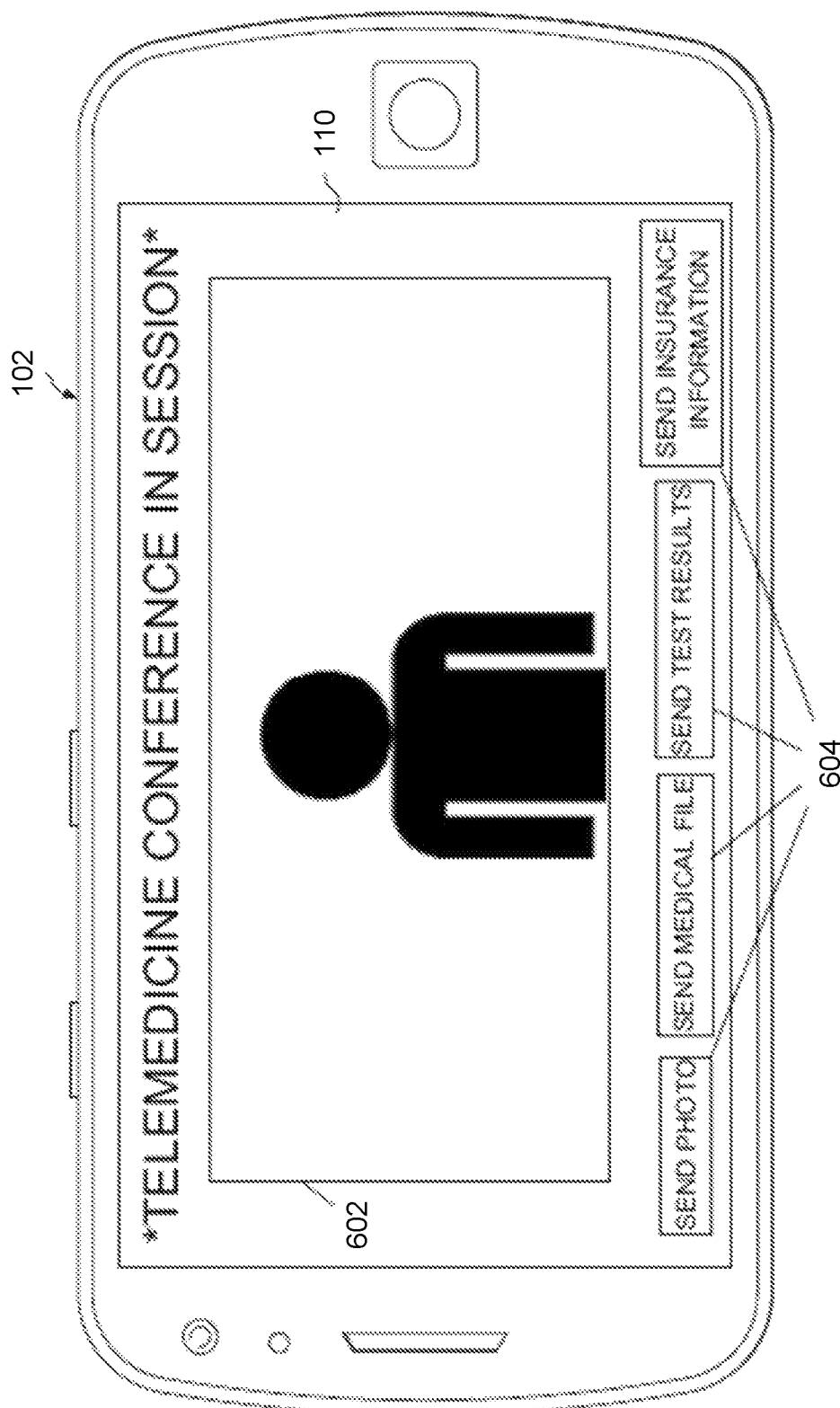
FIG. 6 illustrates one embodiment of a telemedicine conference session on a mobile device.

Referring now to FIG. 6, there is illustrated one embodiment of a telemedicine conference session on a mobile device. During a telemedicine conference that has been initiated as described herein, the user is presented with a video conference window 602 on the display 110. The video conference window 602 allows for user to see the physician that is providing the telemedicine services to the user. It will be understood that the physician may have a similar video window on the device being used by the physician that allows the physician to see the user. This allows the physician to make some visual observations of the user's condition. In addition to the video conference window 602, the user is presented with a plurality of actions 604 on the display 110. The plurality of action 604 may be buttons that allow the user to provide the physician with further information. For example, one button may allow for the user to send a photograph to the physician, such as a photograph of the user's symptoms, or of the user's test results presented on the testing device. One button may also provide an option for sending the user's medical file to the physician, so that the physician can review the user's medical history or other important information. This medical file may include all the information accumulated from all tests performed by the user under the system described herein, and may also include all other medical history information.

The user may have provided a copy of his or her medical history, or such may have been retrieved from a central electronic medical records system.

Other actions that may be provided in the plurality of actions 604 may be a button to send test results to the physician. This would allow the user to send the test results of the latest test the user took before initiating the telemedicine conference, or it may allow for the user to choose the test. The plurality of actions 604 may also include a button for sending the user's insurance information to the physician. The user may have provided this information within the mobile application and had it stored to the server, or this information may have been pulled via a confidential link from a centralized database for the user based on the user's identification information. This option allows the user to give the physician insurance information so that the physician can use the user's insurance for reimbursement of the telemedicine services, and may even set up reimbursement to the user for certain services or products, such as the testing device used for the test.

Figure 7:
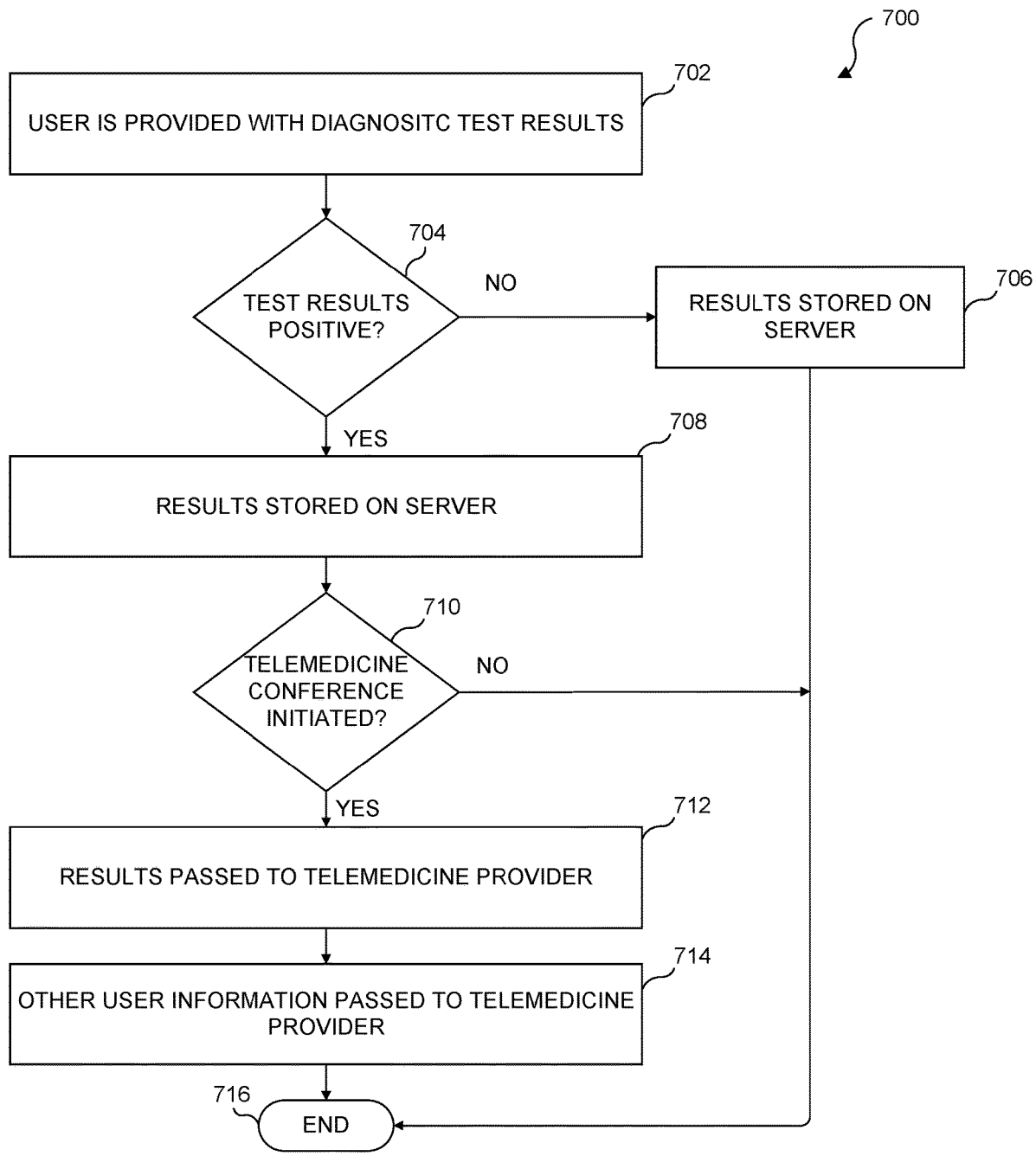
FIG. 7 illustrates a flowchart of one embodiment of a medical file handoff process.

Referring now to FIG. 7, there is illustrated a flowchart of one embodiment of a medical file handoff process 700. The process 700 starts at step 702 where a user is provided with diagnostic test results at the conclusion of a performance of a test. At decision block 704, it is determined whether the test results provide a positive result. If not, at step 706 the results are stored on the server of the system described herein and the process ends at end block 716. If the results are positive, the process flows to step 708 where the results are stored on the server. At step 710, it is determined whether a telemedicine conference has been initiated. This may have been automatically initiated due to the results provided, or may have been initiated in some other way. If the telemedicine conference was not initiated, the process ends at end block 716. If the telemedicine conference was initiated, the process flows to step 712 where the test results are passed to the telemedicine provider participating in the telemedicine conference. The process then flows to step 714, where other user information is passed to the telemedicine provider. The process then ends at end block 716.

The passing of the results to the telemedicine provider and other information at steps 712 and 714 may be performed by the user's mobile device, wherein the mobile device sends the files to the telemedicine provider. The passing may also be done by the server of the system described herein, wherein the results and other information were previously stored to the server and the server then passes the results and other information to the telemedicine provider as a result of the server being notified of a telemedicine conference initiation. The other user information of step 714 may be any information needed by the telemedicine provider, such as past medical records and medical history of the user, past test results, insurance information, or any other information.

Figure 8:
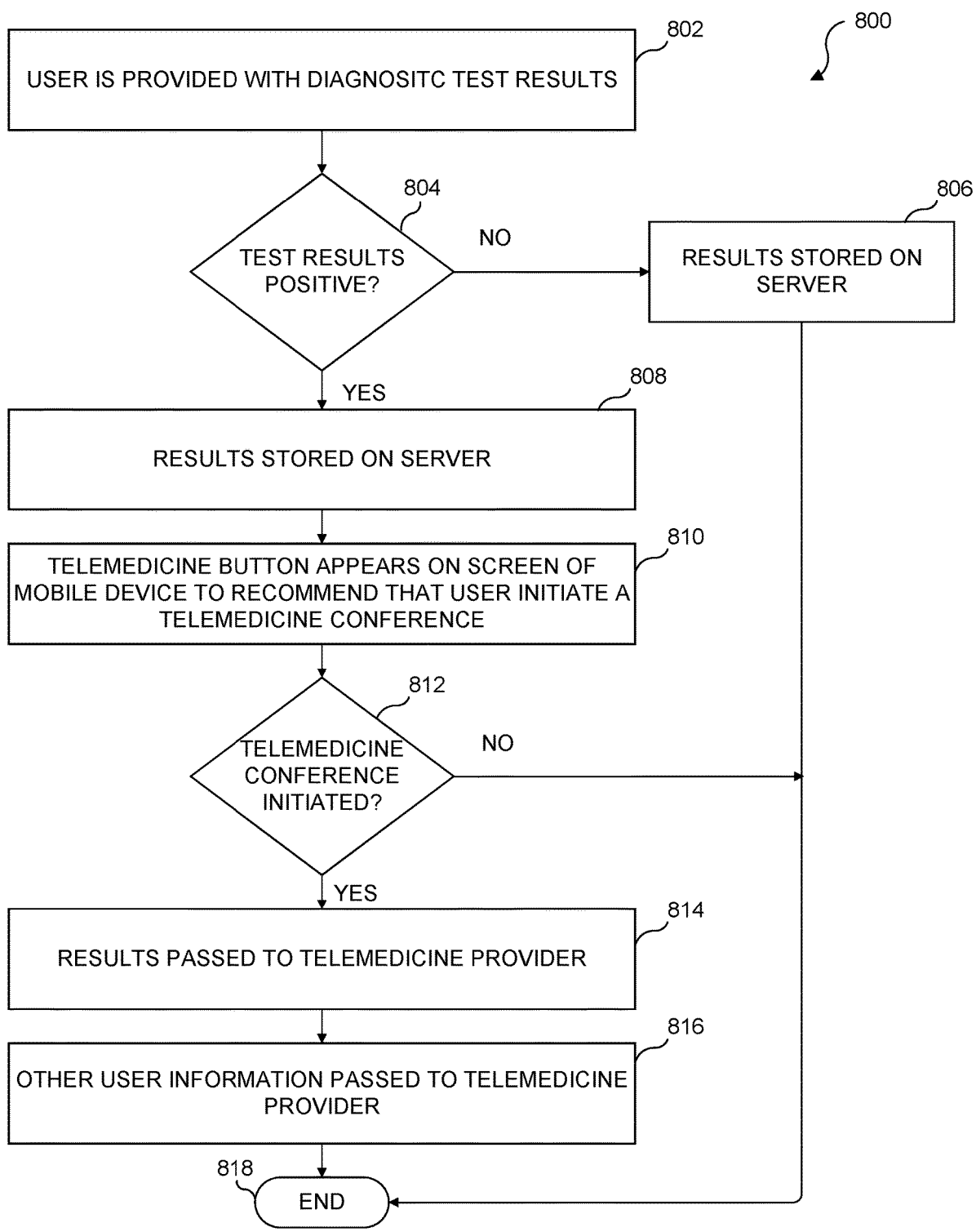
FIG. 8 illustrates a flowchart of one embodiment of a telemedicine conference initiation process.

Referring now to FIG. 8, there is illustrated a flowchart of one embodiment of a telemedicine conference initiation process 800. The process 800 starts at step 802 where a user is provided with diagnostic test results at the conclusion of a performance of a test. At decision block 804, it is determined whether the test results provide a positive result. If not, at step 806 the results are stored on the server of the system described herein and the process ends at end block 818. If the results are positive, the process flows to step 808 where the results are stored on the server. At step 810 a telemedicine button is presented to the user on the screen of the mobile device, similar to that shown in FIG. 28. This button recommends to the user that the user initiate a telemedicine conference, since the test results indicate a positive reaction. At step 812, it is determined whether a telemedicine conference has been initiated. This may have been automatically initiated due to the results provided, or may have been initiated in some other way. If the telemedicine conference was not initiated, the process ends at end block 818. If the telemedicine conference was initiated, the process flows to step 814 where the test results are passed to the telemedicine provider participating in the telemedicine conference. The process then flows to step 816, where other user information is passed to the telemedicine provider. The process then ends at end block 818.

The passing of the results to the telemedicine provider and other information at steps 814 and 816 may be performed by the user's mobile device, wherein the mobile device sends the files to the telemedicine provider. The passing may also be done by the server of the system described herein, wherein the results and other information was previously stored to the server and the server then passes the results and other information to the telemedicine provider as a result of the server being notified of a telemedicine conference initiation. The other user information of step 816 may be any information needed by the telemedicine provider, such as past medical records and history of the user, past test results, insurance information, or any other information.

Figure 9A:
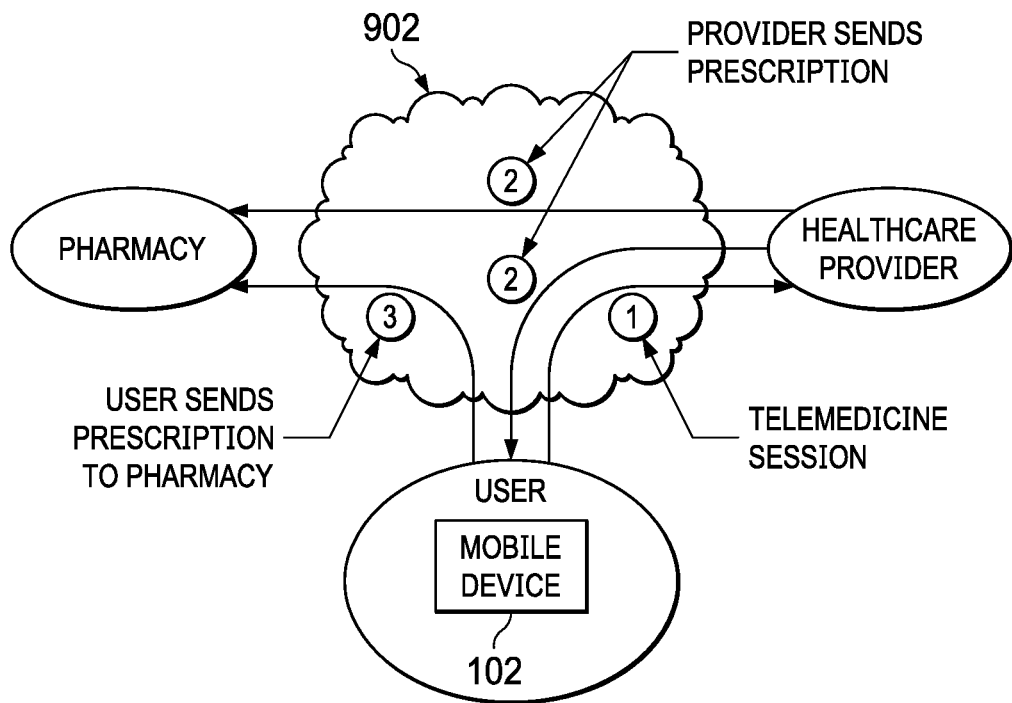
FIGS. 9A and 9B illustrate systems for transmitting prescriptions to a pharmacy using telemedicine.

Referring now to FIG. 9A, there is illustrated an embodiment of a system in which a prescription is transmitted to a pharmacy using a medical test and telemedicine. In these embodiments, rather than the patient needing to physically travel to a pharmacy to drop off a prescription to be filled, the user uses a mobile application to electronically transmit the prescription information to the pharmacy. These embodiments improve upon embodiments which use medical tests and telemedicine and take advantage of the fact that the user is already engaged in a telemedicine session with the user's healthcare provider through a network 902 such as the internet. In these embodiments, the user engages in a telemedicine session with a healthcare provider as described herein, via Path ①. When the user and the healthcare provider complete the telemedicine session, the healthcare provider can prescribe necessary medicine to the mobile application user. However, since the user is not physically present with the healthcare provider, the user does not pick up a physical prescription slip. Instead, the healthcare provider transmits via Path ② the prescription in electronic form either to the user's mobile application, or to the pharmacy of the user's choice. If the healthcare provider transmits the "electronic prescription" to the user's mobile application, then the user can then store the electronic prescription on his mobile device 102 in the mobile application until he is ready to get the prescription filled. The user then uses the mobile application to send the electronic prescription to the pharmacy via Path ③. The pharmacy then fills the prescription as normal.

Figure 9B:
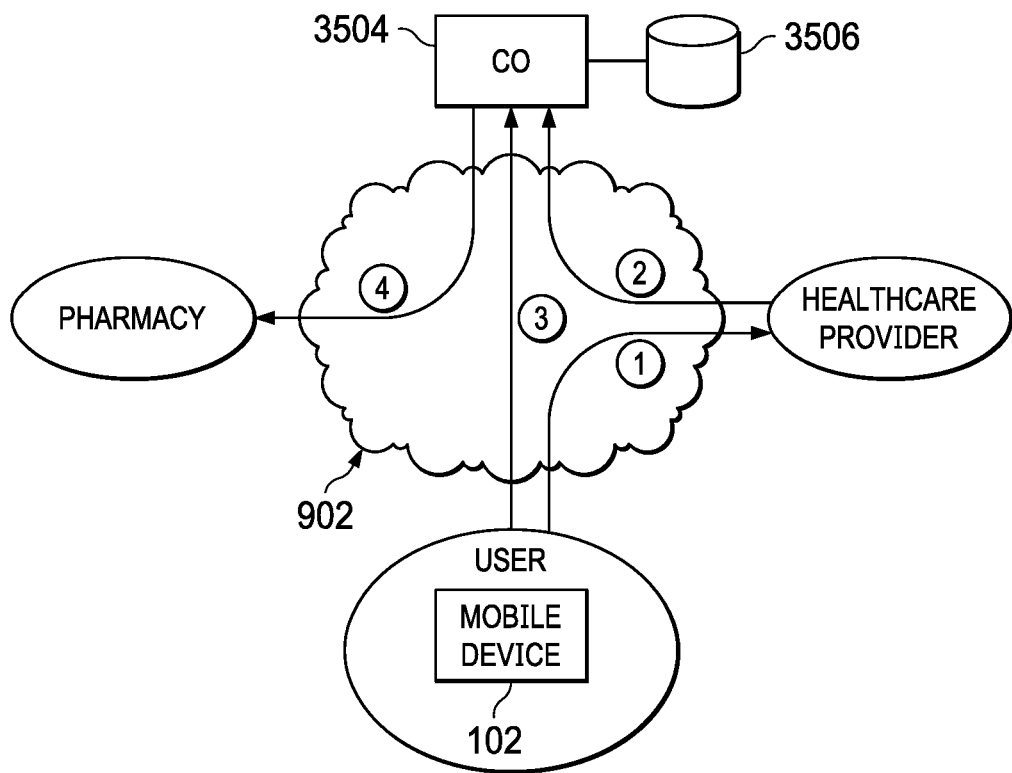

Referring now to FIG. 9B, there is illustrated another embodiment of a system in which a prescription is transmitted to a pharmacy using a medical test and telemedicine. These embodiments are similar to those described herein with respect to FIG. 9A. The system includes a user with a mobile device 102 running a mobile application, a healthcare provider, a pharmacy, and a remote server or central office with a records database. In these embodiments, the user participates in a telemedicine session with a healthcare provider via Path ① as described herein. Next, if the healthcare provider decides that a prescription is needed, the healthcare provider creates a prescription record and transmits the record through a network 902 such as the internet to a central office 904 or remote server via Path ②. The central office 904 then stores the record in a records database 906. When the user is ready to have their prescription filled, they use the mobile application on the mobile device 102 to contact the central office 904 via Path ③. The central office 904 then retrieves the prescription record from the database 906 and sends the prescription record to the pharmacy via Path ④ to have the prescription filled. With this method, the healthcare provider does not have to worry about which pharmacy to send the prescription to, and the fact that the prescription record does not have to be stored on the mobile device 102 means that the user could potentially access the prescription record from another mobile device or any other compatible device with network access.

Figure 10:
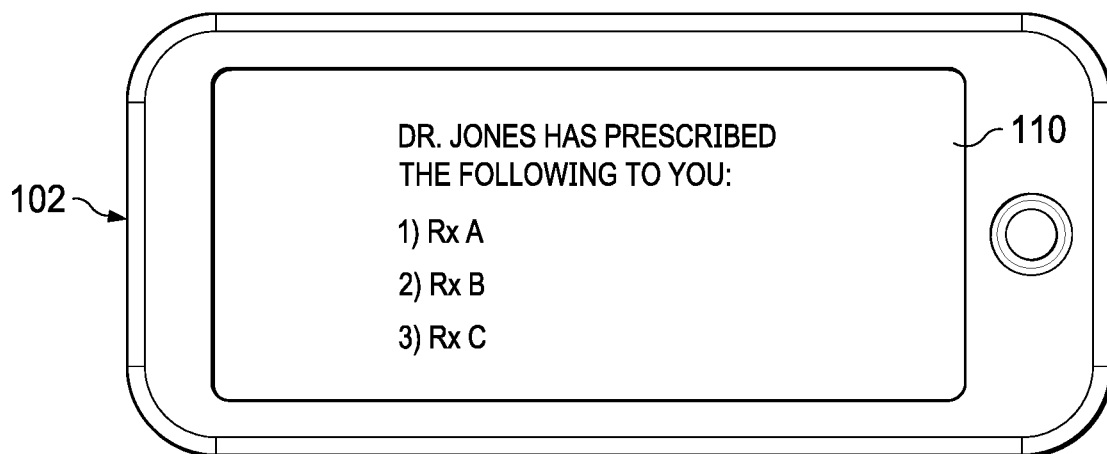
FIG. 10 illustrates an embodiment which uses a mobile application to inform the user which prescriptions have been prescribed

Referring now to FIG. 10, there is illustrated an embodiment in which the mobile application running on the mobile device 102 displays what prescriptions have been prescribed by the healthcare provider to the user. In these embodiments, the mobile application informs the user what prescriptions have been issued or "written" for him by the healthcare provider without the need of physical records. The user receives a notification from the mobile application when the healthcare provider has given the prescription. For example, if the healthcare provider issues ("writes") the prescription during the telemedicine session, the screen illustrated in FIG. 10 will be presented at that time. Or, if the healthcare provider writes the prescription after the telemedicine session has ended, the user will be notified by the mobile application at that time.

Figure 11:
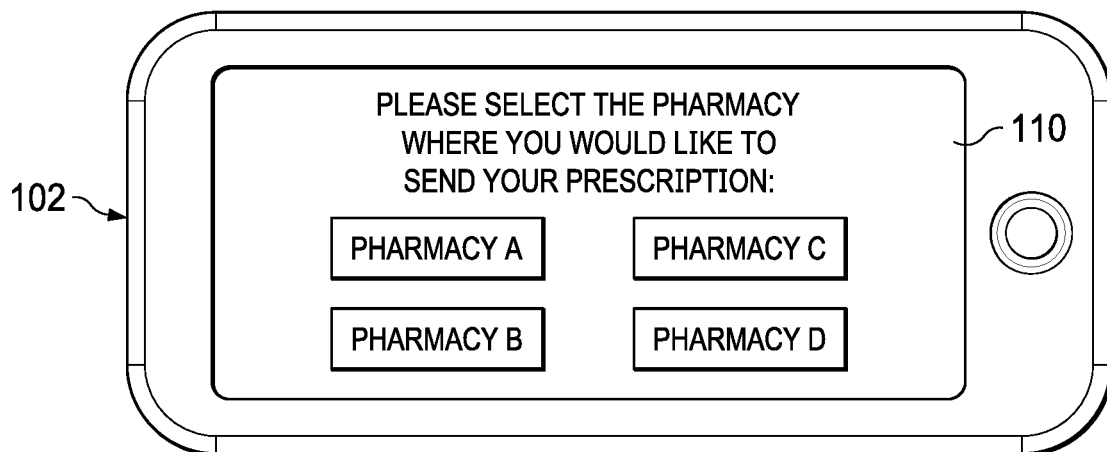
FIG. 11 illustrates an embodiment which uses a mobile application to let a user decide which pharmacy will fill a prescription.

Referring now to FIG. 11, there is illustrated a mobile device 102 from an embodiment in which the user can select which pharmacy to send the prescription to. In these embodiments, a menu displays a choice of pharmacies. These choices can be based on geographic location, on which pharmacies accept the user's insurance, or any other factor which might influence a user's choice of pharmacy. Once the user selects which pharmacy will fill the prescription, the prescription record is transmitted to that pharmacy so that it can be filled. In some embodiments, a preferred pharmacy is selected ahead of time, so that the user does not have to select a pharmacy each time the user receives a prescription from a healthcare provider. In these embodiments, the user is presented instead with a confirmation screen which user will use to send the prescription to the previously-chosen pharmacy to be filled.

Figure 12:
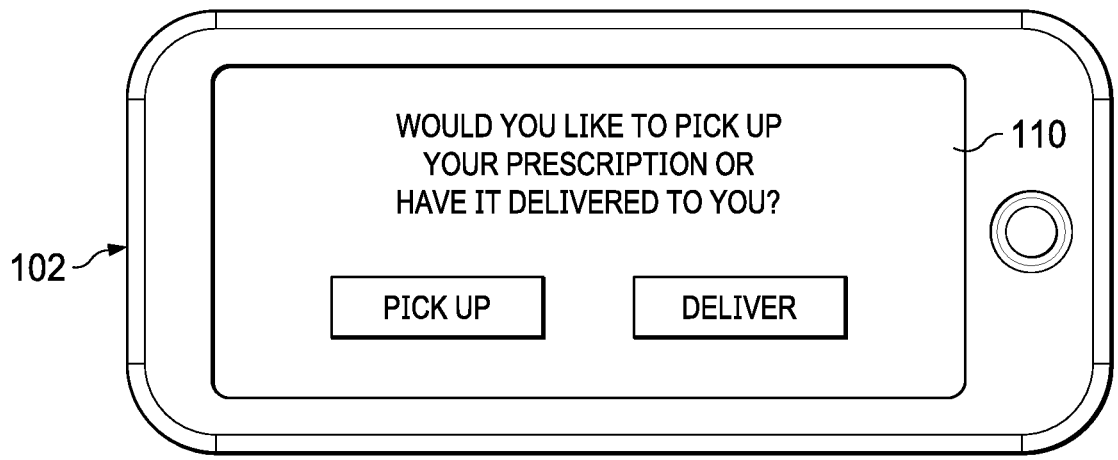
FIG. 12 illustrates an embodiment in which the user can select on a mobile application whether to pick up a prescription or have the prescription delivered.

Referring now to FIG. 12, there is illustrated a mobile device 102 from an embodiment of the system which allows for the prescription to either be picked up or delivered. In some embodiments of the system, the user is offered the convenience of having the prescription delivered to the user's home or place of work. In these embodiments, when a prescription is sent to a pharmacy to be filled, the user is presented with a menu in the mobile application which gives him the option of choosing to pick up the prescription himself, or of having the prescription delivered. If the user selects to have the prescription delivered, the user will then be presented with a screen in the mobile application where he or she enters the delivery address. Some embodiments will allow for addresses to be pre-entered into the mobile application and saved. This will speed up future prescription fillings, as the user will not have to enter the delivery address every time he selects to have a prescription delivered. In some embodiments, if the user selects to pick up the prescription, the user will be given an estimated ready time for the prescription or a notification through the mobile application when the prescription is ready to be picked up.

Figure 13:
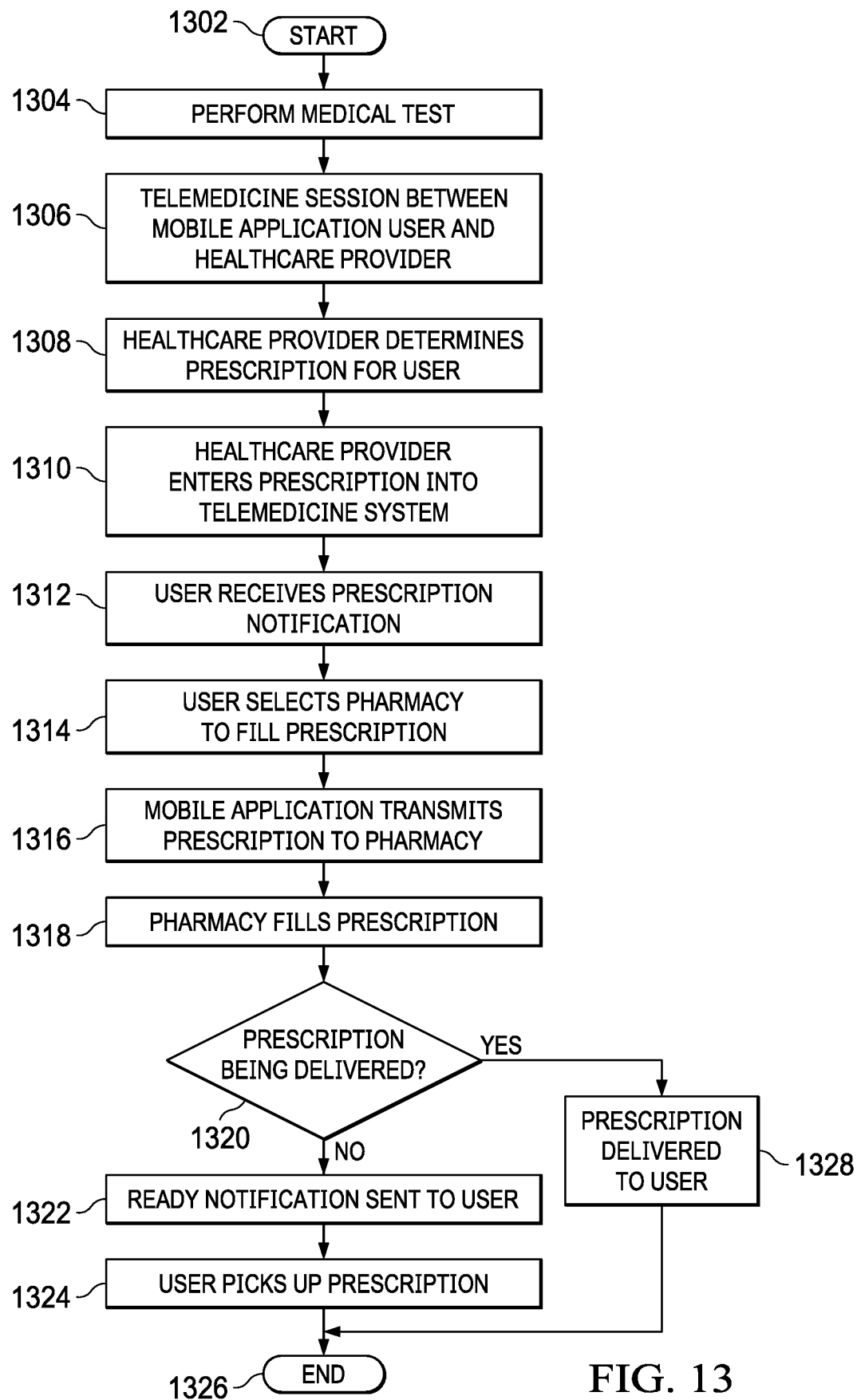
FIG. 13 illustrates a flowchart depicting a process for filling a prescription using a medical test and a telemedicine session.

Referring now to FIG. 13, there is illustrated a flowchart of the process for using a medical test and telemedicine to obtain a prescription. The process starts at Start block 1302 and proceeds to block 1304. At block 1304, the user performs a medical test such as is described herein. Next, at block 1306, a telemedicine session is established and occurs between the user and a healthcare provider as described herein. Next, the process moves to block 1308, where the healthcare provider determines that the user needs a prescription. In some embodiments, this step takes place during the telemedicine session. Next, the process moves to block 1310, where the healthcare provider issues a prescription for the user and enters the prescription information into the telemedicine system. Next, at block 1312, the user is notified through the mobile application that they have been prescribed medication. The process then moves to block 1314, where the user selects a pharmacy to fill the prescription. This step may not take place if the user has a pharmacy pre-selected. Next, at block 1316, the mobile application causes the prescription to be sent to the pharmacy to be filled. The process then moves to block 1318, where the pharmacy fills the prescription. The block then moves to decision block 1320, where the user chooses whether the prescription will be picked up or delivered. If the user chooses to pick up the prescription, the process moves to function block 1322, where the system sends the user a notification that the prescription is ready for pick-up. The process moves to block 1324, where the user picks up the prescription and then ends at block 1326. If the user chooses to have the prescription delivered, then the process moves to block 1328, where the prescription is delivered to the user at his selected address. The process then ends at block 1326.

Figure 14:
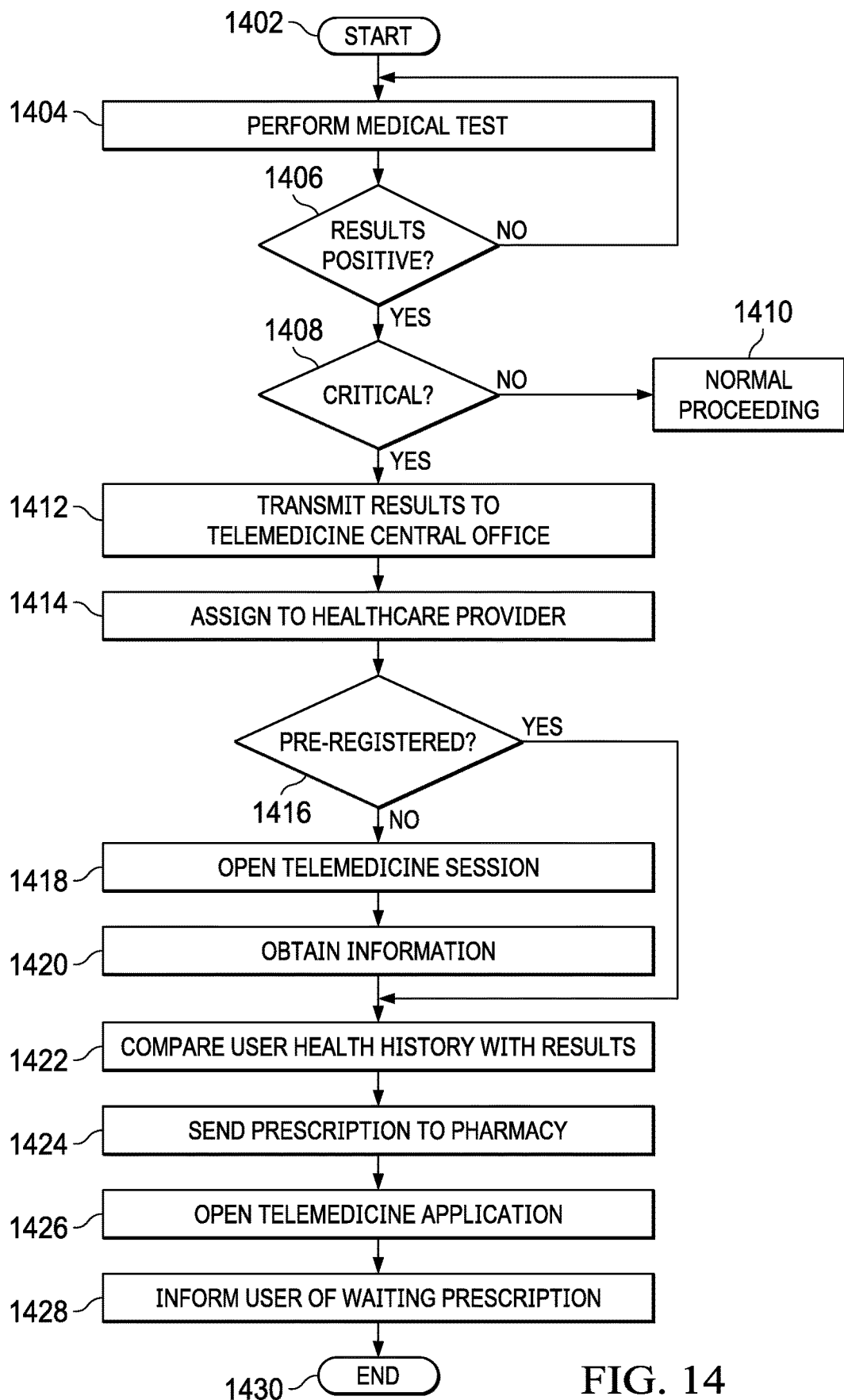
FIG. 14 illustrates an embodiment in which a telemedicine mobile application is used to automatically fill a prescription.

Referring now to FIG. 14, there is illustrated an embodiment in which a telemedicine mobile application is used to automatically fill a prescription. In some cases, when a patient is diagnosed with a particular ailment, the prescription is likely to be a predetermined medication or set of medications. In these cases, a healthcare provider can often issue a prescription for the user without having to actually see or talk to the user. Having a user's health history and the results of a diagnostic test are often enough for a healthcare provider to issue a prescription for a user. Some embodiments take advantage of these situations and improve the efficiency of the telemedicine and prescription-filling process by allowing prescriptions to be issued and filled automatically, without significant interaction between the user and the healthcare provider. The process starts at Start block 1402 and proceeds to function block 1404, where the user performs a medical test. The process then moves to decision block 1406. If the medical test returns negative results, the process loops back to block 1404 until the user performs another medical test sometime in the future. If the test results are positive, the process moves to decision block 1408. If the positive result from the test does not indicate a "critical" or urgent situation, the process movies to block 1410, where a normal telemedicine proceeding occurs, as described herein. If, however, the results indicate an urgent or critical situation which can be resolved without significant user interaction with a healthcare provider, the process moves to function block 1412. At block 1412, the mobile application transmits the medical test results to a central office or remote server for the telemedicine system. The process moves to block 1414, where a healthcare provider is assigned to the user's test results, which are transmitted by the central office to the healthcare provider. The process then moves to decision block 1416, where, if the user has pre-registered, that is, has supplied their health history and pharmacy preferences to the telemedicine system, the process moves to block 1422, where the healthcare provider compares the user's health history with the medical test results to determine if a prescription should (can) be issued to the user.

If, at block 1416, the user has not pre-registered, the process moves to block 1418, where a session of the telemedicine application is opened on the user's mobile device. This session is simply for the user to provide the information necessary for the healthcare provider to issue the proper prescription. The process moves to block 1420, where the user provides their health history and their pharmacy preferences to the telemedicine system through the mobile application. Next, the process move to block 1422, where the healthcare provider compares the user's health history and the test results to determine if a prescription should be issued. The process then moves to block 1424, where the healthcare provider issues a prescription and sends it to the pharmacy. The process moves next to block 1426, where the telemedicine application opens on the user's mobile device. At block 1428, the telemedicine mobile application informs the user that the prescription has been filled by the pharmacy and is ready for pick-up or delivery. The process then ends at End block 1430.

Referring now to FIG. 15, there is illustrated an embodiment of a system which utilizes a remote diagnostic test to initiate a medical escalation and intervention. In some situations, the result of a medical diagnostic test will indicate that immediate or urgent medical attention is needed for the patient. In some embodiments, medical attention will be summoned automatically in these situations. In these embodiments, the user performs a medical medical test and uses a mobile application running on a mobile device 102 to capture an image of the test product, as described herein. The mobile application then transmits, via Path ①, the test information through a network 1502 to a remote server or central office 1504. The central office 1504 accesses a database 1506 for the necessary information to generate a result for the medical test. The central office 1504 may also retrieve from the database 1506 criteria for determining whether or not a medical escalation or intervention is warranted on the basis of the test results. The central office 1504 generates a test result and checks the criteria to determine if medical escalation is needed. If no medical escalation is needed, the central office 1504 simply returns, via Path ②, the test results to the mobile device 102 through the network 1502. If, however, the central office 1504 determines that some type of medical escalation is warranted, then the central office transmits, though the network 1502 via Path ③, the test and test result information, along with information about the user (such as any relevant personal, demographic and/or contact information collected from the user) to a healthcare provider 1508. Alternatively, instead of the healthcare provider 1508 being contacted by the central office 1508, in some embodiments, the fact that a medical escalation is needed is transmitted along with the test results from the central office 1502 through the network 1502 via Path ② to the mobile device 102 running the mobile application. The mobile device 102 then transmits the test and test result information to a healthcare provider 1508 through the network 1502 via Path ④.

The manner of the medical escalation or intervention varies depending on the embodiment, and may vary depending on the type of test and/or the test results. In some embodiments, the escalation takes the form of notifying emergency medical personnel, rather than a healthcare provider 1508, of an urgent medical situation. In these embodiments, the central office may call 911 or in some other way notify emergency services These embodiments would be useful, for example, if a blood test shows that the medical test user has near fatal levels blood sugar or that the user is having a heart attack or stroke. In other embodiments, the medical escalation takes the form of the mobile application on the mobile device automatically initiating a telemedicine session with a healthcare provider 1508. These embodiments are useful, for example, in urgent, but not quite emergency, situations. For example, elevated blood sugar or high blood pressure might not be immanently deadly to a patient, but should still be addressed and brought to the attention of a healthcare 1508 provider quickly. In other embodiments which are most useful for urgent—but not quite emergency—situations, the central office 1504 notifies the healthcare provider 1508 of the test results, and leaves it up to the healthcare provider to determine the best next course of action to take with respect to the patient.

Referring now to FIG. 16, there is illustrated an example of a table which would be found in the database of a central office 1506 and which contains criteria for when to initiate a medical intervention based on the results of a remote diagnostic test. The table 1602 includes several columns of information. In the example embodiment depicted in FIG. 16, the diagnostic test is a quantitative one which produces a numerical rating as part of the test result, similar to the embodiments described herein. An example of such a test could be a blood glucose test, wherein a certain risk is generally associated with a range of glucose levels. In this example, a low test result "rating" indicates a low health risk for the condition being tested, while a higher "rating" indicates a higher risk. In the some embodiments which use a table such as table 1602, different types of medical intervention are used for different test results. The first column 1604 of table 1602 specifies a range of test result "ratings," while the rest of the columns 1604, 1606, and 1608 specify information correlating to that rating range. Column 1606 specifies the health risk associated with a particular test result rating from column 1604, and column 1608 specifies what type of medical intervention will be initiated for a test result within a given range. For example, if a user conducts the example medical test, and the central office 1504 generates a test result rating of 57 (which indicates a dangerous health risk), then the central office will not only return the test result to the user, it will also initiate an urgent medical intervention, such as initiating a telemedicine session between the user and a healthcare provider. If the central office 1504 generates a test result rating of 93 (which would indicate a deadly health risk), then the central office will initiate an emergency health intervention, such as notifying emergency medical services of the user's condition. On the other hand, if the test result rating is in the "NORMAL" or "ELEVATED" range, then no medical intervention will be initiated, and the central office 1504 will simply return the test results to the user and the mobile device 102. Naturally, other embodiments will have different styles of tables in the central office 1504 database. Some embodiments which have qualitative rather than quantitative tests (for example, testing simply "positive" or "negative" for a disease) will not have various multiple different types of medical intervention.

Referring now to FIG. 17, there is illustrated a mobile device 102 from an embodiment in which a medical intervention in the form of a telemedicine session is initiated on a mobile device in response to a diagnostic test. In the example illustrated in FIG. 17, the mobile application running on the mobile device 102 displays that a medical test performed by a user has returned a result showing the user has dangerous levels of blood glucose. As described herein, different embodiments will have different types of medical intervention. In the example of FIG. 17, the mobile application automatically initiates a telemedicine session in response to the high blood glucose test result. The mobile application informs the user that the test results indicated a dangerous glucose level, initiates the telemedicine session, and transmits the test results to the healthcare provider (some embodiments transmit the test results to the healthcare provider directly from the central office 1504).

Figures 18, 19:
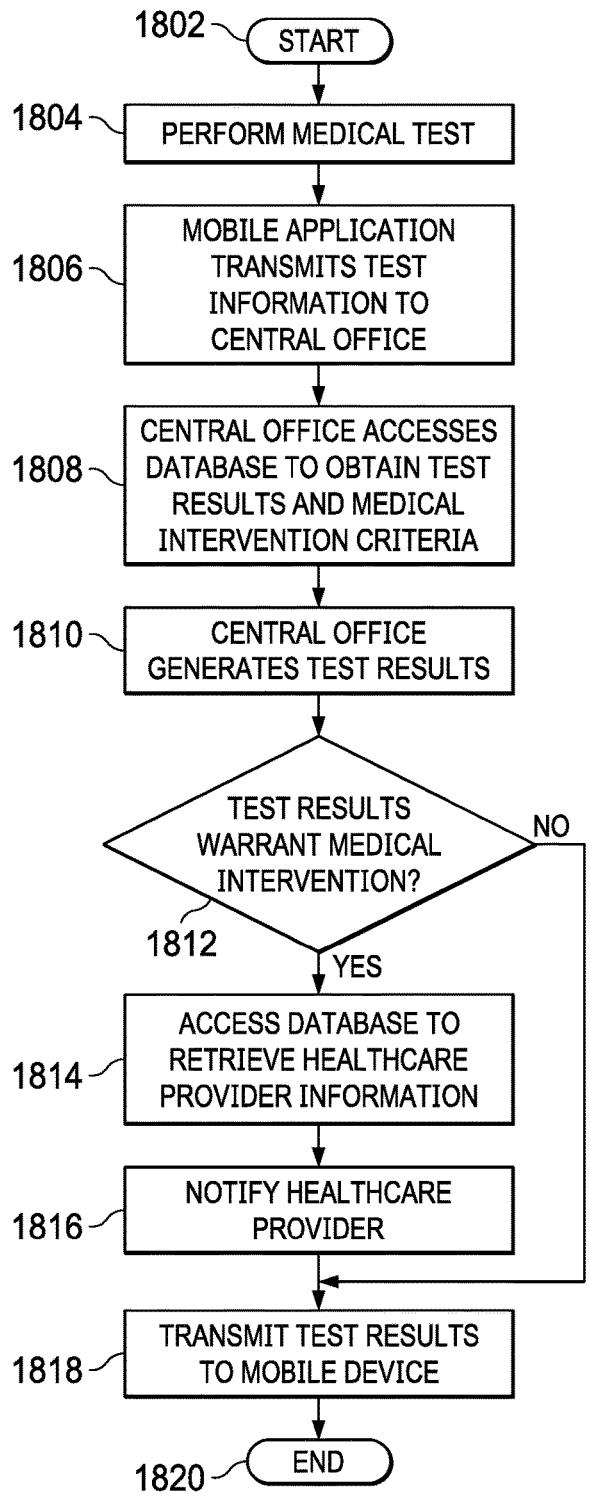
FIG. 18 illustrates a flowchart for an embodiment which initiates a medical escalation or intervention as a result of a remote diagnostic test.
FIG. 19 illustrates an embodiment which includes mapping a diagnostic test to an individual user to create a unique profile on a remote database.

Referring now to FIG. 18, there is illustrated a flowchart for an embodiment which initiates a medical escalation or intervention as a result of a remote diagnostic test. The process starts at START block 1802. Next, the process moves to function block 1804, where the user performs a medical medical test and reads the testing equipment with a mobile device, such as is described herein. Next, at block 1806, a mobile application on the mobile device transmits the test information, including the image or images of the captured by the mobile device, to a central office over a network 1502. The process flows to block 1808, where the central office 1504 accesses a connected database 1506 to obtain information for generating a test result, as well as information detailing the criteria for initiating a medical intervention. Next, at block 1810, the central office 1504 generates test results based on the information transmitted from the mobile device 102 and the information obtained from the database 1506. At decision block 1812, the central office 102 determines whether or not, based on test results, a medical intervention is warranted. If a medical intervention is warranted, the process flows to block 1814, where the central office accesses the database 1506 to retrieve healthcare provider information for the user. The process then proceeds to block 1816, where the central office 1504 notifies the healthcare provider 1508 of the test results. Next, the process moves to block 1818, where the central office 1504 transmits the test results to the mobile device 102 through the network 1502. The process then ends at END block 1820. If, at decision block 1812, no medical intervention is warranted, then the process instead moves to block 1818 and block 1820, as described herein.

Referring next to FIG. 19, there is illustrated an embodiment which includes mapping a diagnostic test to an individual user to create a unique profile on a remote database. Each time a patient conducts a medical test, there is a change to gather information about that patient and the patient's test. Instead of each piece of information about a patient or a test being regarded individually, multiple data points and pieces of information for a common patient can be associated with each other, providing a greater insight into and creating a detailed profile of the patient. Referring to FIG. 19, there is illustrated a unique profile record 1900. Each unique profile record 1900 is associated with an individual patient or diagnostic test user and has a unique ID 1902. The unique profile record 1900 contains information associated with the patient/user, such as the patient name 1904, the name of a healthcare provider 1906 associated with the patient, or the name of a pharmacy 1908 associated with the patient. Importantly, the unique profile record 1900 also includes the biologic IDs 1910 associated with the user. Each biologic ID 1910 is the same ID as the biologic header 2002 in one of the unique biologic ID database tables 2000. Thus, the unique profile record 1900 includes a "link" to the record of each biologic used by the patient associated with the unique profile record. Each time a diagnostic test is conducted on a biologic sample, the biologic sample is associated with the unique profile record 1900, which means the unique biologic ID database table 2000 (which includes data about the test) is associated with the unique profile record 1900 and the user. This means that more information about the patient is collected and accumulated.

Different embodiments will include different types of data to be stored within each unique profile record 1900. In some embodiments, the unique profile record 1900 includes information about food or medications to which the patient is allergic. Some embodiments of the unique profile record 1900 include records of which illnesses which the patient has had. Virtually any type of information related to the patient/user can be included in the unique profile record 1900 in various embodiments, so long as it contributes to construction a better "picture" of the patient/user.

Figure 20:
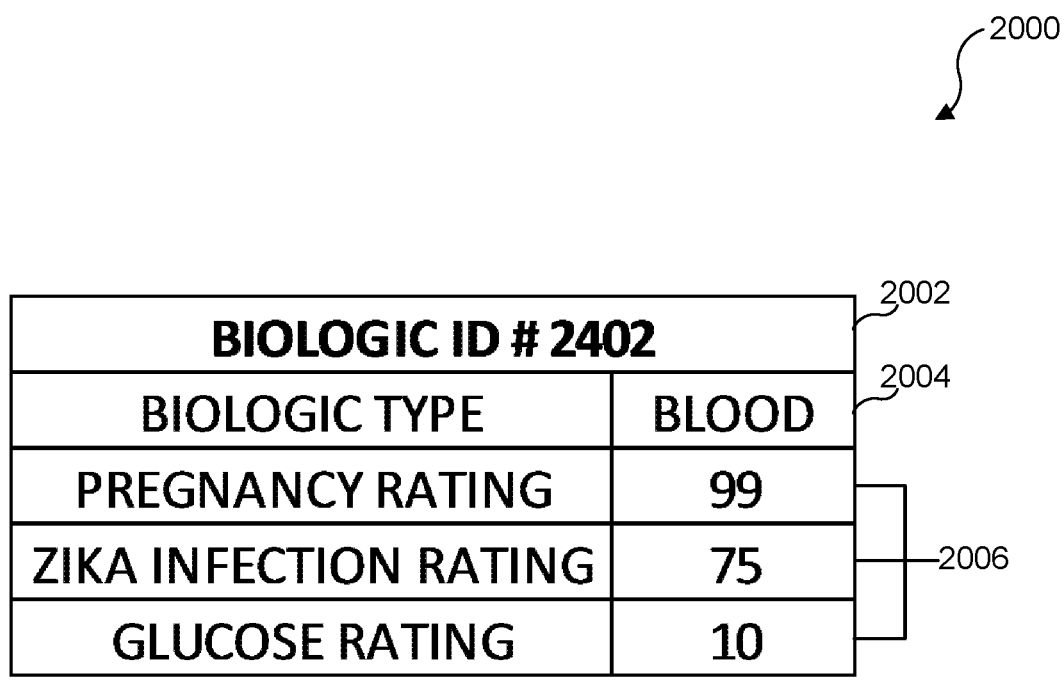
FIG. 20 illustrates an example of a unique biologic ID database table.

Referring now to FIG. 20, there is illustrated an example of a unique biologic ID database table 2000. The table 2000 is illustrative of the type of data stored in association with data for a biologic transmitted by a mobile device 102 for storage on the database 118. A biologic ID header 2002 is provided that shows that the biologic sample has been given a unique ID. All data concerning the biologic may be stored in association with the unique biologic ID. The table 2000 also includes a biologic type entry 2004. This designates what type of biologic that the biologic associated with the unique ID is, such as blood, urine, stool, saliva, sweat, or other biologics. The table 2000 also provides a plurality of test ratings 2006, for various tests performed on the biologic. In the example shown in FIG. 20, a blood biologic is provided having an assigned ID of 2402, and having been testing for pregnancy markers, the Zika virus, and for glucose levels. The rating for pregnancy was a 99 rating, the rating for a Zika infection was a 75, and the rating for glucose levels was a 10. This would indicate that the test subject has an extremely high likelihood of both a pregnancy and a Zika infection, which would have resulted in a warning to seek medical attention at the conclusion of the tests. Other information may also be stored in the database in relation to the biologic, including other condition ratings, time and date each test was performed, user information such as ethnicity, gender, and age, and status indicators such as whether a test subject visited a physician as a result of the tests. The database 118 thus provides the test subject with a growing collection of information that may be accessed by the test subject. This allows the test subject to present the test results to her physician for medical attention or additional testing, and allows for others who may access the database, such as disease researchers, to have access to data on various biologic samples and their markers.

Figure 21:
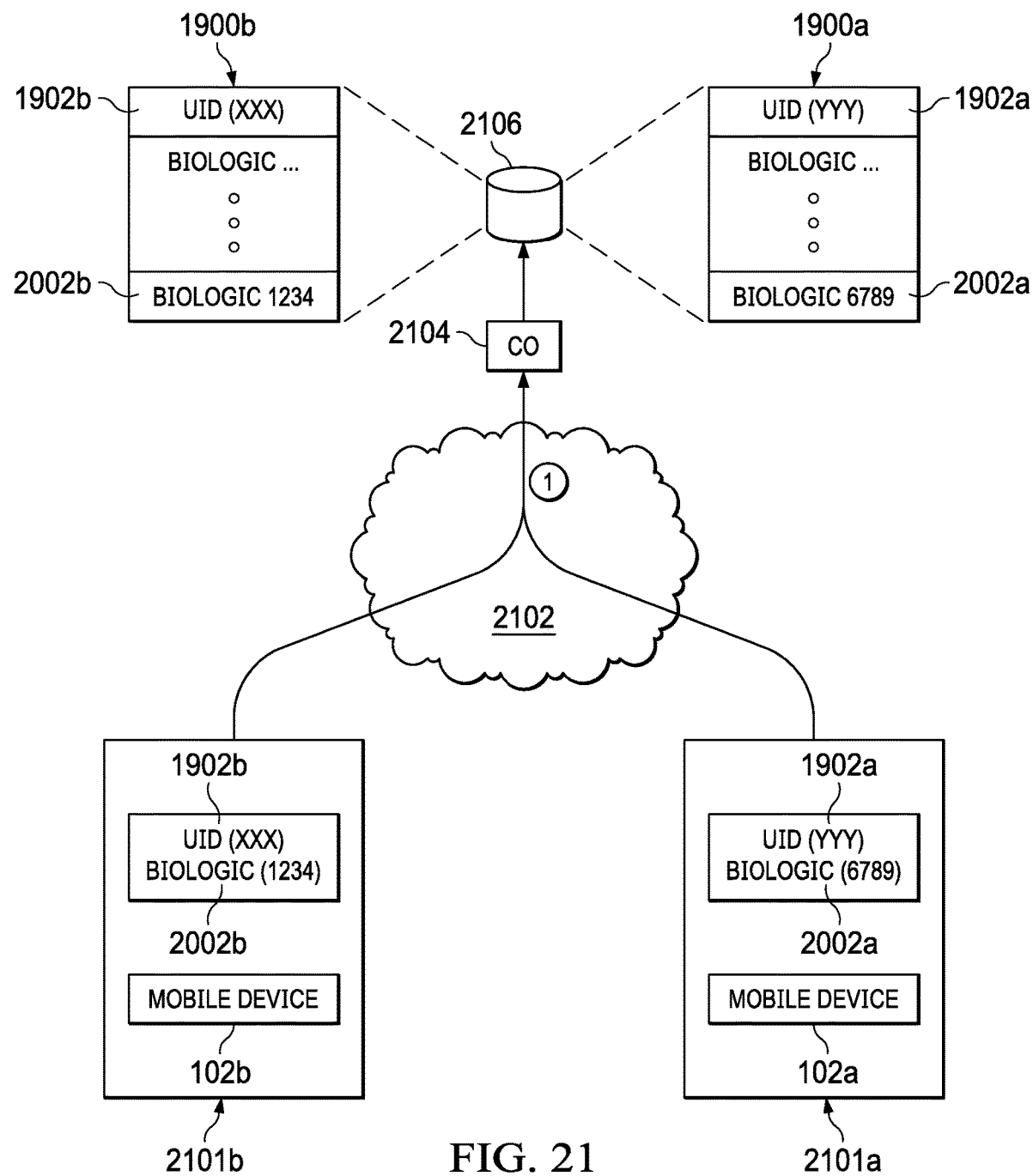
FIG. 21 illustrates an embodiment which includes mapping diagnostic tests to individual users to create unique profiles.

Referring next to FIG. 21, there is illustrated an embodiment which includes mapping diagnostic tests to individual users to create unique profiles. The patient/user 2101 conducts a medical test using a mobile device 102. The first time the patient 2101 uses the mobile application on the mobile device 102, the application allows the patient to create a unique ID 1902 to be assigned to the unique profile record 1900 associated with the patient. In some embodiments, the unique ID 1902 is simply assigned by the mobile application instead of being chosen by the user 2101. After a test is conducted, the mobile application transmits the biologic ID 2002 of the biologic tested along with the unique ID 1902 along Path ① through a network 2102, such as the internet, to a remote server or central office 2104. Once the biologic ID 2002 and the associated unique ID 1902 reaches the central office server 2104, the central office server transmits the biologic ID and the unique ID to a connected database 2106. Within database 2106 are stored the unique profile records 1900 for each patient/user 2101. Once the database 2106 receives the biologic ID 2002 and the unique ID 1902, the database uses the unique ID to identify the correct unique profile record 1900 and then appends the biologic ID 2002 to that unique profile record. If this is the first test conducted for/by a particular patient/user 2101, then the database 2106 creates a new unique profile record 1900 with the provided unique ID 1902 and appends the biologic ID 2002. In this way, each time a user 2101 conducts a diagnostic test, the unique ID 1902 and the biologic ID 2002 are sent to the database 2106, where the unique profile record is incrementally augmented with additional information about the user/patient 2101. In some embodiments, the biologic ID 2002 is not assigned by the application on the mobile device 102. Instead, the mobile device sends the information relating to the biologic (test type, test results, etc.) to the central office serve 2104 and database 2106, which then assign a biologic ID 2002 to the biologic data and associate it with the appropriate unique ID 1902.

Data for other users 2101 with other unique profiles 1902 will be handled similarly. Since each user 2101 has a unique profile record 1900 associated with him or her, the database 2106 will be able to associated biologic IDs 2002 with the correct user. In this way, the database 2106 will be populated with unique profile records 1900, from which potentially vast amounts of data can be obtained.

Figure 22:
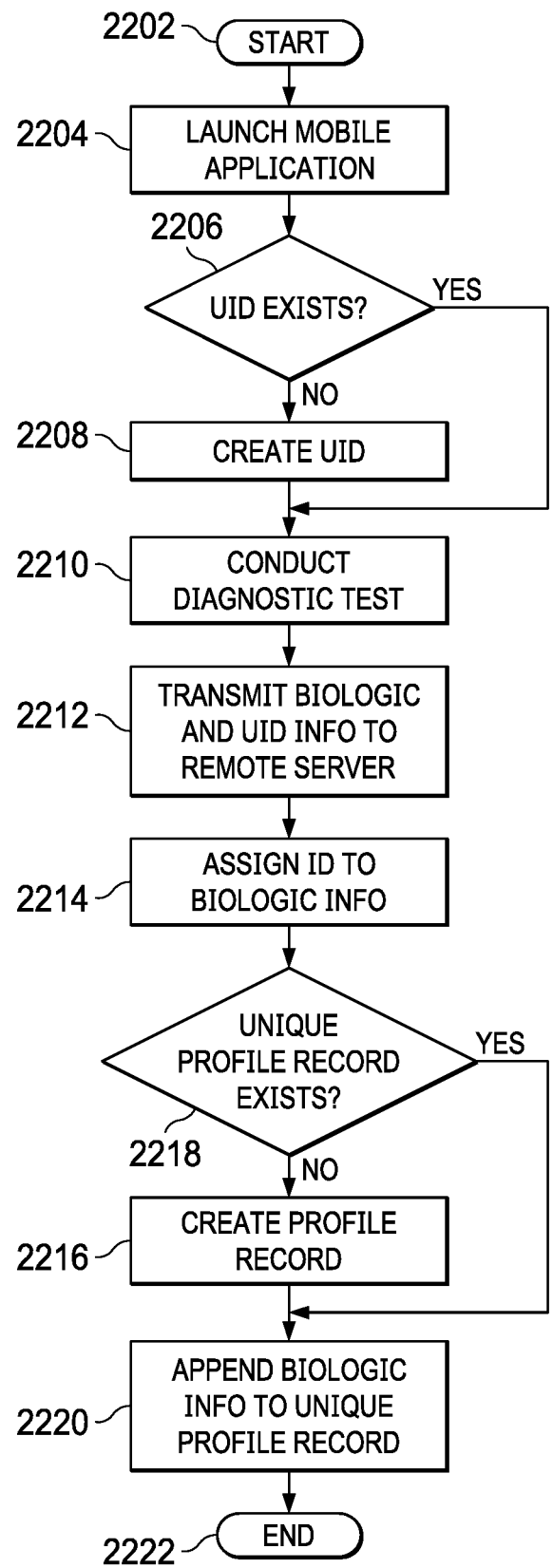
FIG. 22 illustrates a flowchart for an embodiment which includes mapping a diagnostic test to an individual user to create a unique profile on a remote database.

Referring now to FIG. 22, there is illustrated a flowchart for an embodiment which includes mapping a diagnostic test to an individual user to create a unique profile on a remote database. The process starts at Start block 2202 and proceeds to function block 2204, where the user launches the mobile application on the mobile device 102. The process then moves to decision block 2206. If a unique ID 1902 for the user does not exist, the process moves to function block 2208, where a unique ID is created by the mobile application. The process then moves to function block 2210. If, at block 2206, a unique ID 1902 for the user does exist, the process skips block 2208 and moves to function block 2210. At block 2210, the user conducts a diagnostic test with a testing device 300 and a mobile device 102 as described herein. The process then moves to block 2212, where the mobile application transmits the biologic ID information 2002 (which will also link the user to data about the type of diagnostic test) and the unique ID 1902 to the remote server 2104. At step 2214, an ID is assigned to the biologic information. The process then moves to decision block 2218. If a unique profile record 1900 for the user does not exist, the process moves to function block 2216, where a unique profile record is created. The process then moves to function block 2220. If, at decision block 2218, a unique profile record 1900 for the user already exists, the process moves to block 2220. At block 2220, the database 2106 appends the biologic ID information 2002 to the unique profile record 1900. The diagnostic test performed by the user is now mapped to the user's profile 1900 through the biologic database ID table 2000. The process then ends at End block 2222.

Figure 23:
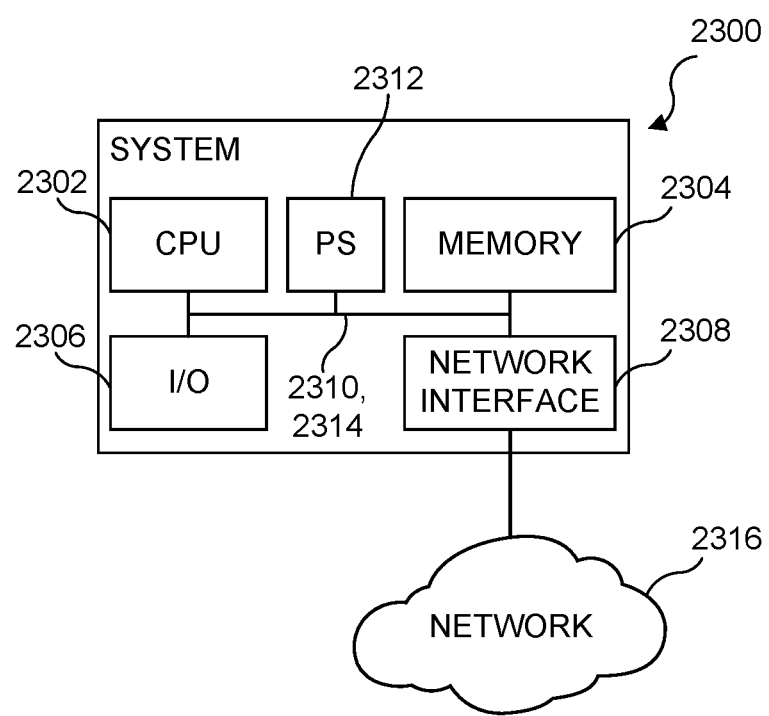
FIG. 23 illustrates a diagrammatic view of one embodiment of a system device that may be used within the environment described herein.

Referring to FIG. 23, one embodiment of a system device 2300 is illustrated. The system device 2300 is one possible example of a device used by an end user, and/or a device such as the mobile device 102 or the server 116. Embodiments include cellular telephones (including smart phones), personal digital assistants (PDAs), netbooks, tablets, laptops, desktops, workstations, telepresence consoles, and any other computing device that can communicate with another computing device using a wireless and/or wireline communication link. Such communications may be direct (e.g., via a peer-to-peer network, an ad hoc network, or using a direct connection), indirect, such as through a server or other proxy (e.g., in a client-server model), or may use a combination of direct and indirect communications. It is understood that the device may be implemented in many different ways and by many different types of systems, and may be customized as needed to operate within a particular environment.

The system 2300 may include a controller (e.g., a central processing unit ("CPU")) 2302, a memory unit 2304, an input/output ("I/O") device 2306, and a network interface 2308. The components 2302, 2304, 2306, and 2308 are interconnected by a transport system (e.g., a bus) 2310. A power supply (PS) 2312 may provide power to components of the computer system 2300, such as the CPU 2302 and memory unit 2304, via a power system 2314 (which is illustrated with the transport system 2310 but may be different). It is understood that the system 2300 may be differently configured and that each of the listed components may actually represent several different components. For example, the CPU 2302 may actually represent a multi-processor or a distributed processing system; the memory unit 2304 may include different levels of cache memory, main memory, hard disks, and remote storage locations; the I/O device 2306 may include monitors, keyboards, and the like; and the network interface 2308 may include one or more network cards providing one or more wired and/or wireless connections to a network 2316. Therefore, a wide range of flexibility is anticipated in the configuration of the computer system 2300.

The system 2300 may use any operating system (or multiple operating systems), including various versions of operating systems provided by Microsoft (such as WINDOWS), Apple (such as Mac OS X), UNIX, and LINUX, and may include operating systems specifically developed for handheld devices, personal computers, servers, and embedded devices depending on the use of the system 2300. The operating system, as well as other instructions, may be stored in the memory unit 2304 and executed by the processor 2302. For example, the memory unit 2304 may include instructions for performing some or all of the methods described herein.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A method of signaling a medical response action, the method comprising:
   receiving a biofluidic input by a logical testing unit, wherein the logical testing unit comprising a testing display and a persistent testing mechanism;
   determining whether the logical testing unit is able to process the biofluidic input responsive to one or more analogical data processors of the logical testing unit;
   responsive to a determination that the logical testing unit is able to process the biofluidic input, processing, by a persistent testing mechanism of the logical testing unit, at least a portion of the biofluidic input;
   generating one or more logical results from the biofluidic input;
   displaying, on a testing display of the logical testing unit, the one or more logical results;
   capturing one or more logical indicators on the testing display indicating the one or more logical results with a mobile computing unit, wherein the mobile computing unit includes a mobile display;
   generating by a client or application a unique identifier responsive to the captured one or more logical indicators, the unique identifier containing at least a first portion including the one or more logical results and a second portion associated with the mobile computing unit;
   sending the unique identifier via a network, to a central processing unit; and
   processing the unique identifier by the central processing unit to determine a treatment response action responsive to the one or more logical results contained in the unique identifier; and
   initiating a treatment action responsive to the determined treatment response action.

2. The method of claim 1, wherein:
   determining whether the logical testing unit is able to process the biofluidic input further comprises:
   determining a type of the biofluidic input,
   wherein the type of the biofluidic input is a bodily compound.

3. The method of claim 2, wherein:
   processing, by the persistent testing mechanism, at least a portion of biofluidic data of the biofluidic input further comprises:
   assigning a biofluidic logic input to the biofluidic input; and
   assigning a persistent antibody logic input to one or more persistent antibodies; and
   wherein generating one or more logical results from the biofluidic data from the biofluidic input comprises combining the biofluidic logic input to at least one of the persistent antibody logic inputs via a logic gate.
   wherein the logic gate is one of OR, AND, XOR, NOR, NAND or NOT.

4. The method of claim 3, wherein:
   the biofluidic logic input is 0 or 1; and
   the persistent antibody logic input is 0 or 1.

5. The method of claim 2, wherein:
   the treatment response action is at least one of product referral, prescriptive filing, home delivery, medical professional contacted, emergency response, prescriptive authority, medical professional referral or initiating medical professional video.

6. The method of claim 2, wherein:
   the bodily compound is at least one of saliva, blood, urine, feces or semen.

7. The method of claim 1, wherein:
   capturing the logical indicators on the testing display with the mobile computing unit is via a rear facing camera or a front facing camera.

8. A method of signaling a medical response action, the method comprising:
   receiving a biofluidic input by a logical testing unit;
   determining one or more test results from the biofluidic input;
   generating, by a mobile computing unit, a unique identifier responsive to the determined one or more test results, the unique identifier containing at least a first portion including the one or more test results, a second portion associated with a test subject and a third portion associated with the mobile computing unit;

processing the unique identifier to determine a treatment response action responsive to the one or more test results contained in the unique identifier; and triggering a treatment action in response to the treatment response action.

9. The method of claim 8, wherein:

the treatment response action is at least one of a product referral, a prescriptive filing, a home delivery, a medical professional contacted, a emergency response, a prescriptive authority, a medical professional referral or initiating a medical professional video.

10. The method of claim 8, wherein:

the biofluidic input is at least one of saliva, blood, urine, feces or semen.

11. The method of claim 8, wherein:

the treatment response action is at least one of a product referral, a prescriptive filing, a home delivery, a medical professional contacted, a emergency response, a prescriptive authority, a medical professional referral or initiating a medical professional video.

12. A method of signaling a medical response action, the method comprising:

receiving, at a central processing unit, a unique identifier generated responsive to one or more test results generated by a logical testing unit from a client or application, the unique identifier including a first portion identifying the one or more test results by the logical testing unit, a second portion associated with a test subject tested by the logical testing unit and a third portion associated with a computing unit containing the client or application;

determining, by the central processing unit, responsive to the unique identifier the one or more test results identified by the unique identifier;

determining, by the central processing unit, a treatment action responsive to the one or more test results identified by the unique identifier and the second portion of the unique identifier associated with the test subject;

generating, by the central processing unit, a treatment response actuator responsive to the determined treatment action; and providing, by the central processing unit, the treatment response actuator to the computing unit containing the client or application.

* * * * *